United States Patent
Moser et al.

(10) Patent No.: US 10,059,710 B2
(45) Date of Patent: Aug. 28, 2018

(54) STABLE FORMULATIONS OF 5,10-METHYLENE-(6R)-TETRAHYDROFOLIC ACID

(71) Applicant: MERCK & CIE, Schaffhausen (CH)

(72) Inventors: Rudolf Moser, Schaffhausen (CH); Viola Groehn, Dachsen (CH); Thomas Egger, Wangi (CH); Thomas Ammann, Marthalen (CH)

(73) Assignee: MERCK & CIE, Schaffhausen (CH)

( * ) Notice: Subject to any disclaimer, the term of this patent is extended or adjusted under 35 U.S.C. 154(b) by 0 days.

(21) Appl. No.: 15/435,787

(22) Filed: Feb. 17, 2017

(65) Prior Publication Data

US 2017/0233394 A1  Aug. 17, 2017

Related U.S. Application Data

(60) Provisional application No. 62/296,296, filed on Feb. 17, 2016.

(51) Int. Cl.
| | |
|---|---|
| *A61K 9/08* | (2006.01) |
| *A61K 31/519* | (2006.01) |
| *A61K 9/19* | (2006.01) |
| *C07D 475/12* | (2006.01) |

(52) U.S. Cl.
CPC .............. *C07D 475/12* (2013.01); *A61K 9/08* (2013.01); *A61K 9/19* (2013.01); *A61K 31/519* (2013.01); *C07B 2200/13* (2013.01)

(58) Field of Classification Search
CPC .......... A61K 31/519; A61K 9/08; A61K 9/19; C07B 2200/13; C07D 475/12
See application file for complete search history.

(56) References Cited

U.S. PATENT DOCUMENTS

| | | | |
|---|---|---|---|
| 2,300,505 | A | 11/1942 | Hubbard |
| 4,931,441 | A | 6/1990 | Lawrence |
| 5,300,505 | A | 4/1994 | Muller et al. |
| 5,434,087 | A | 7/1995 | Beggs et al. |
| 5,989,566 | A | 11/1999 | Cobb et al. |
| 5,997,915 | A | 12/1999 | Bailey et al. |
| 6,613,767 | B1 | 9/2003 | Nijkerk et al. |
| 9,180,128 | B2 | 11/2015 | Moser et al. |
| 2002/0052374 | A1 | 5/2002 | Rabelink et al. |
| 2002/0183277 | A1 | 12/2002 | Binderup |
| 2007/0099866 | A1 | 5/2007 | Moser |
| 2016/0030573 | A1 | 2/2016 | Moser |
| 2016/0185787 | A1 | 6/2016 | Moser |

FOREIGN PATENT DOCUMENTS

| | | | | |
|---|---|---|---|---|
| CN | | 1842337 A | 10/2006 | |
| EP | | 0537492 A2 | 4/1993 | |
| WO | | 95/26963 A1 | 10/1995 | |
| WO | | 97/27764 A1 | 8/1997 | |
| WO | WO 2015/022407 | * | 2/2015 | ........... C07D 475/24 |

OTHER PUBLICATIONS

E. Odin et al., "Chemical Stability and Human Plasma Pharmacokinetics of Reduced Folates", Cancer Investigation, vol. 16, No. 7 (1998) pp. 447-455.

* cited by examiner

*Primary Examiner* — Erich A Leeser

(74) *Attorney, Agent, or Firm* — Millen White Zelano and Branigan, PC; Csaba Henter

(57) ABSTRACT

The invention is directed towards stable formulations of 5,10-methylene-(6R)-tetrahydrofolic acid and its hemisulfate salt as well as pharmaceutical compositions and uses thereof in therapy, preferably chemotherapy.

33 Claims, 13 Drawing Sheets

Fig. 10

Stability testing program of the hemisulfate salt of 5,10-methylene-(6R)-tetrahydrofolic acid

| relative content | = relative content of 5,10-methylene-(6R)-tetrahydrofolic acid compared to the starting value at t = 0, HPLC measurement |
| --- | --- |
| 10-CHO-H4PteGlu | = 10-formtertahydrofolic acid, HPLC [%w/w], stability marker |

| Lot Nr. LMTH-3605 | | period [months] | 0 | 3 | 6 | 9 | 12 | 18 | 24 | 36 |
| --- | --- | --- | --- | --- | --- | --- | --- | --- | --- | --- |
| +25°C/60% relative humidity | relative content | | 100.00 | 99.71 | 99.53 | 99.59 | 99.21 | 99.25 | 99.41 | 98.46 |
| | 10-CHO-H4PteGlu | | 0.24 | 0.47 | 0.67 | 0.73 | 0.77 | 0.87 | 0.94 | 0.98 |
| +40°C/75% relative humidity | Content | | 100.00 | 99.50 | 99.32 | 99.18 | 98.77 | | | |
| | 10-CHO-H4PteGlu | | 0.24 | 0.83 | 1.01 | 1.14 | 1.23 | | | |
| +5°C | relative content | | 100.00 | 99.81 | 99.87 | 99.88 | 99.84 | 99.61 | 99.83 | 98.78 |
| | 10-CHO-H4PteGlu | | 0.24 | 0.29 | 0.33 | 0.37 | 0.42 | 0.42 | 0.55 | 0.57 |
| -20°C/60% relative humidity | relative content | | 100.00 | 99.74 | 99.93 | 99.77 | 99.14 | 99.77 | 99.83 | 98.92 |
| | 10-CHO-H4PteGlu | | 0.24 | 0.27 | 0.27 | 0.39 | 0.31 | 0.25 | 0.37 | 0.35 |

| Lot Nr. LMTH-3606 | | period [months] | 0 | 3 | 6 | 9 | 12 | 18 | 24 | 36 |
| --- | --- | --- | --- | --- | --- | --- | --- | --- | --- | --- |
| +25°C/60% relative humidity | relative content | | 100.00 | 99.95 | 99.95 | 100.06 | 99.67 | 99.38 | 99.42 | 99.02 |
| | 10-CHO-H4PteGlu | | 0.19 | 0.53 | 0.59 | 0.70 | 0.78 | 0.89 | 1.00 | 1.11 |
| +40°C/75% relative humidity | relative content | | 100.00 | 99.58 | 99.44 | 99.40 | 99.05 | | | |
| | 10-CHO-H4PteGlu | | 0.19 | 0.94 | 1.18 | 1.29 | 1.41 | | | |
| +5°C | Content | | 100.00 | 100.16 | 100.17 | 100.29 | 100.07 | 99.63 | 99.91 | 99.67 |
| | 10-CHO-H4PteGlu | | 0.19 | 0.34 | 0.30 | 0.37 | 0.37 | 0.40 | 0.46 | 0.47 |
| -20°C/60% relative humidity | relative content | | 100.00 | 100.10 | 100.34 | 100.30 | 100.15 | 99.94 | 99.76 | 100.00 |
| | 10-CHO-H4PteGlu | | 0.19 | 0.30 | 0.22 | 0.30 | 0.27 | 0.31 | 0.32 | 0.26 |

| Lot Nr. LMTH-0002 | | period [months] | 0 | 3 | 6 | 9 | 12 | 18 | 24 | 36 |
| --- | --- | --- | --- | --- | --- | --- | --- | --- | --- | --- |
| +25°C/60% relative humidity | relative content | | 100.00 | 99.50 | 99.46 | 99.44 | 99.06 | 98.99 | 98.96 | |
| | 10-CHO-H4PteGlu | | 0.25 | 0.64 | 0.73 | 0.84 | 0.94 | 1.05 | 1.19 | |
| +40°C/75% relative humidity | relative content | | 100.00 | 98.88 | 98.91 | 98.72 | 98.36 | | | |
| | 10-CHO-H4PteGlu | | 0.25 | 1.11 | 1.31 | 1.51 | 1.77 | | | |
| +5°C | relative content | | 100.00 | 99.83 | 99.84 | 99.84 | 99.62 | 99.18 | 99.55 | |
| | 10-CHO-H4PteGlu | | 0.25 | 0.42 | 0.37 | 0.50 | 0.51 | 0.54 | 0.56 | |
| -20°C/60% relative humidity | relative content | | 100.00 | 99.78 | 100.01 | 99.91 | 99.68 | 99.37 | 99.54 | |
| | 10-CHO-H4PteGlu | | 0.25 | 0.38 | 0.29 | 0.42 | 0.42 | 0.42 | 0.39 | |

STABLE FORMULATIONS OF 5,10-METHYLENE-(6R)-TETRAHYDROFOLIC ACID

This application relates to US application having the Ser. No. 14/912,328, filed on Feb. 16, 2016, having the title: New Stable Salt of 5,10-methylene-(6R)-tetrahydrofolic acid, and having the same inventorship as the present application.

The invention is directed towards 5,10-methylene-(6R)-tetrahydrofolic acid [(6R)-5,10-$CH_2$-THF] and its hemisulfate salt, which is preferably in crystalline form, but may also be non-crystalline, e.g., substantially or fully amorphous, and may be present in a dissolved form, e.g. in a solution, and preferably towards pharmaceutical compositions and uses thereof in therapy, preferably chemotherapy. Preferably, the formulations are those formulations having an enhanced stability, which formulations preferably contain citrate, or formulations containing another buffer, or another buffer in combination with citrate. Further preference is given to formulations that have a slightly acidic to basic pH, preferably a physiological pH. Even further preference is given to lyophilisates prepared from said hemisulfate salt or solutions from said hemisulfate salt and to formulations reconstituted from a lyophilisate prepared from said hemisulfate salt of 5,10-methylene-(6R)-tetrahydrofolic acid or solutions thereof. The stabilization of the formulations of (6R)-5,10-$CH_2$-THF can be achieved without additions of reducing agents (antioxidants) and without the exclusion of atmospheric oxygen, and the resultant formulations, e.g., solutions or lyophilisates, exhibit stabilization for months in solid isolated form at ambient temperature, also for months as lyophilisate at ambient temperature, for days in suspension even at elevated temperature, for hours as reconstituted lyophilisate at ambient temperature. Embodiments include all of the stabilized formulations, their lyophilisates, as well as their reconstituted solution forms from said lyophilisates along with their methods of preparation and use.

The term hemisulfate as it refers to said salt of the 5,10-methylene-(6R)-tetrahydrofolic acid means that the molar ratio between the 5,10-methylene-(6R)-tetrahydrofolic acid and the $H_2SO_4$ moieties is 2:1 or about 2:1, meaning, e.g., with a variation of plus-minus 20%, e.g., 1.6 to 2.4 of 5,10-methylene-(6R)-tetrahydrofolic acid moieties present per sulfate moiety, or plus-minus 10%, e.g., 1.8 to 2.2 of 5,10-methylene-(6R)-tetrahydrofolic acid moieties present per sulfate moiety, or plus-minus 5%, e.g., 1.9 to 2.1 of 5,10-methylene-(6R)-tetrahydrofolic acid moieties present per sulfate moiety, or plus-minus 2%, e.g., 1.96 to 2.04 of 5,10-methylene-(6R)-tetrahydrofolic acid moieties present per sulfate moiety, or plus-minus 1%, e.g., 1.98 to 2.02 of 5,10-methylene-(6R)-tetrahydrofolic acid moieties present per sulfate moiety.

The term sulfate as it refers to said salt of the 5,10-methylene-(6R)-tetrahydrofolic acid means that the molar ratio between the 5,10-methylene-(6R)-tetrahydrofolic acid and the $H_2SO_4$ moieties is 1:1 or about 1:1, meaning, e.g., with a variation of plus-minus 20%, e.g., 0.8 to 1.2 of 5,10-methylene-(6R)-tetrahydrofolic acid moieties present per sulfate moiety, or plus-minus 10%, e.g., 0.9 to 1.1 of 5,10-methylene-(6R)-tetrahydrofolic acid moieties present per sulfate moiety, or plus-minus 5%, e.g., 0.95 to 1.05 of 5,10-methylene-(6R)-tetrahydrofolic acid moieties present per sulfate moiety, or plus-minus 2%, e.g., 0.98 to 1.02 of 5,10-methylene-(6R)-tetrahydrofolic acid moieties present per sulfate moiety, or plus-minus 1%, e.g., 0.99 to 1.01 of 5,10-methylene-(6R)-tetrahydrofolic acid moieties present per sulfate moiety.

The reduced folate (6R)-5,10-$CH_2$-THF is known for its efficacy as a cytostatic agent and has been preferably administered in combination with fluorinated pyrimidines, such as 5-fluorouracil (5-FU), in the treatment of solid tumors (Seley, K. L. IDrugs 4 (1), 99, 2001). (6R)-5,10-$CH_2$-THF achieves its chemotherapeutic effect together with the base analogue and 5-FU metabolite 5-FdUMP by inhibiting the enzyme thymidylate synthase (TS). TS catalyses the conversion of deoxyuridylate (dUMP) to deoxythymidylate (dTMP), which is an essential building block for DNA synthesis. Deactivation of TS occurs by formation of a covalent, ternary inhibition complex between TS, the base analogue 5-FdUMP, which is a metabolite of 5-FU, and (6R)-5,10-$CH_2$-THF. An enhancement of the cytotoxic effect of 5-FU can be achieved by increasing the intracellular concentration of (6R)-5,10-$CH_2$-THF, whereupon the stability of the ternary complex is increased. This causes direct inhibition of DNA synthesis and repair, which ultimately results in cell death and delay of tumor growth.

However, there are undesirable properties associated with (6R)-5,10-$CH_2$-THF that limit its pharmaceutical use. For example, (6R)-5,10-$CH_2$-THF is highly susceptible to oxidation and chemical degradation that results in unfavorably high impurity levels. It is well known that to be amenable for pharmaceutical use an active agent (such as (6R)-5,10-$CH_2$-THF) needs to fulfill several requirements including (i) high chemical and isomeric stability of the active agent itself as well as pharmaceutical compositions thereof, such that effective storage over an acceptable period of time can be achieved, without exhibiting a significant change in the active agent's physicochemical characteristics, (ii) high chemical and isomeric purity of the active agent, (iii) ease of handling and processing of the active agent to allow transfer of the active agent into suitable formulations, etc.

5,10-methylenetetrahydrofolic acid is an addition product of tetrahydrofolic acid and formaldehyde (see e.g. Poe, M. et al. Biochemistry 18 (24), 5527, 1979; Kallen, R. G. Methods in Enzymology 18B, 705, 1971) and is known for its extremely high sensitivity to oxidation by air as well as instability in neutral and/or acidic environments potentially leading to chemical degradation and/or hydrolysis (see e.g. Odin, E. et al., Cancer Investigation 16 (7), 447, 1998; Osborn, M. J. et al., J. Am. Chem. Soc. 82, 4921, 1960; Hawkes, J., and Villota, R. Food Sci. Nutr. 28, 439, 1989). Attempts to stabilize 5,10-methylenetetrahydrofolates included e.g. (i) rigorous exclusion of atmospheric oxygen by the use of special technical devices for the reconstitution of solid formulations and the injection of 5,10-methylenetetrahydrofolates in an air-free environment (see e.g. Odin, E. et al., Cancer Investigation 16 (7), 447, 1998; U.S. Pat. No. 4,564,054); (ii) addition of a reducing agent such as L(+)-ascorbic acid or salts thereof, reduced gamma-glutathione, beta-mercaptoethanol, thioglycerol, N-acetyl-L-cysteine, etc. as an antioxidant for the highly sensitive 5,10-methylenetetrahydrofolic acid and for tetrahydrofolic acid in particular; (iii) stabilization by means of cyclodextrin inclusion compounds (see e.g. EP 0 579 996 B1); (iv) addition of citrate while adjusting the pH to a basic value (see e.g. EP 1 641 460 B1); or (v) formation of various salts such as the sulfate salt (see e.g. EP 0 537 492 B1).

Nevertheless, there still remains a great need for stabile (6R)-5,10-$CH_2$-THF compounds which show high chemical and isomeric purity and/or possess high stability both as compounds as well as when formulated into pharmaceutical compositions, yet may be efficiently prepared, purified and isolated and/or are amenable to manipulation (e.g. acceptable solubility in pharmaceutically acceptable solvents, flowability and particle size) and/or formulation with negligible decomposition or change of the physical and chemical characteristics of the compound, preferably formulated at a high molar percentage (in order to minimize the quantity of material which must be formulated and administered to produce a therapeutically effective dose).

It has now surprisingly been found that transformation of (6R)-5,10-CH$_2$-THF to its hemisulfate salt provides excellent stability to the compound as well as to pharmaceutical compositions thereof and thereby overcomes the previously discussed known drawbacks and allow for the preparation of pharmaceutical compositions if high purity and a low content of either oxidation products or other chemical degradation products. The advantageous stability characteristics of the (6R)-5,10-CH$_2$-THF hemisulfate salt will allow the effective use of this compound in medicinal applications.

Even though the sulfate salt of 5,10-methylene-(6R)-tetrahydrofolic acid was known, there was no way of knowing from the prior art that a hemisulfate salt of this compound is even possible, or how such could be achieved. Moreover, unknown and thus surprising is the unexpected increased stability of the hemisulfate salt, its lyophilisates, and reconstituted products from said lyophilisates. Very surprisingly, when applying an increased temperature of about 50° C. on solutions containing 5,10-methylene-(6R)-tetrahydrofolic acid and sulfuric acid, preferably in an excess amount, including in the range of 30-80° C., preferably 40-60° C., and more preferably 45-55° C. made crystallization to occur from said solution.

Not only could a hemisulfate salt be made but, as an extra bonus, this hemisulfate salt turned out to possess higher chemical stability than the earlier known corresponding sulfate salt (EP 0537492 B1); enough to be formulated into a useful pharmaceutical composition of high purity and stability.

One embodiment is directed in a first aspect to the hemisulfate salt of (6R)-5,10-CH$_2$-THF.

Preferably, the hemisulfate salt of (6R)-5,10-CH$_2$-THF is in chemically and/or isomerically and/or crystalline pure form, more preferably, the hemisulfate salt of (6R)-5,10-CH$_2$-THF is in substantially crystalline form.

In specific embodiments, the hemisulfate salt of (6R)-5,10-CH$_2$-THF is in anhydrous form, thus in a preferred embodiment the hemisulfate salt of (6R)-5,10-CH$_2$-THF is in crystalline anhydrous form.

Preferably, the hemisulfate salt of (6R)-5,10-CH$_2$-THF is in a crystalline form characterized by one or more X-ray pattern peak positions at an angle of diffraction 2theta (2θ) of 4.7°, 17.9°, and 23.3° expressed in 2θ±0.2° 2θ (CuKα radiation).

In specific embodiments the hemisulfate salt of (6R)-5,10-CH$_2$-THF is characterised in that it provides a FT-Raman spectrum containing peaks at wavenumbers (expressed in ±2 cm$^{-1}$) of 1672, 1656, 1603, 1553, 1474, 1301, 637, 624 and 363 cm$^{-1}$.

A further aspect is directed to pharmaceutical compositions comprising a hemisulfate salt of (6R)-5,10-CH$_2$-THF and a pharmaceutically acceptable carrier or diluent, optionally further comprising at least one additional therapeutic agent including but not limited to, bactericides, antibiotics, antivirals, antiseptics, antineoplastics, anticancer compounds such as chemotherapeutic agents, antifungals, and/or anti-inflammatory agents or other bioactive or therapeutic agents that are suitable for human use, in particular anticancer compounds such as chemotherapeutic agents, for example 5-FU and derivatives, and antifolates, e.g. methotrexate, Pemetrexed.

A further aspect is directed to the use of a hemisulfate salt of (6R)-5,10-CH$_2$-THF (or pharmaceutical compositions thereof) in therapy, preferably in cancer chemotherapy.

As used herein, (6R)-5,10-CH$_2$-THF refers to 5,10-methylenetetrahydrofolic acid in its naturally occurring isomeric form (N-[4-[(6aR)-3-amino-1,2,5,6,6a,7-hexahydro-1-oxoimidazo[1,5-f]pteridin-8(9H)-yl]benzoyl]-L-glutamic acid), wherein the chiral centers at C6 of the pteridine ring and the α-carbon of the glutamic acid moiety are in their naturally occurring configuration. Thus, the terms "isomeric purity" resp. "stereoisomeric purity", as used herein, refer to the amount of (6R)-5,10-CH$_2$-THF in a sample, which may contain one or more other isomers of the same compound. The terms "isomerically pure" resp. "stereoisomerically pure", as used herein, mean (6R)-5,10-CH$_2$-THF or its hemisulfate salt in isomeric excess over other isomers greater than about 80%, preferably greater than about 90%, preferably greater than about 95%, more preferably greater than about 97%, even more preferably greater than about 99%, more preferably greater than about 99.5% or more, and most preferably up to 100%, wherein the remainder may be one or more of the other isomers.

The term "crystalline form" (or "polymorph" or "crystal form") as used herein refers to a solid state form which consists of a specific orderly three-dimensional arrangement of structural units. Thus different crystalline forms of the same compound arise from different packing of the molecules in the solid state, which results in different crystal symmetries and/or unit cell parameter. Typically, different solid or crystal forms have one or more different physical and/or chemical property, such as different solubility profiles, different thermodynamic and chemical stabilities, different melting points temperatures and/or different X-ray diffraction patterns, and thus can be distinguished by X-ray diffraction, Infrared (IR) spectroscopy, Differential Scanning calorimetry (DSC), Raman spectroscopy, solid state NMR as well as melting points, density, hardness, optical and electrical properties, stability and/or solubility profile, etc. Little or no regular 3-dimensional arrangement is typically described by the term "amorphous".

The term "crystalline compound" refers to a solid form of (6R)-5,10-CH$_2$-THF or its hemisulfate salt comprising discernible amounts of crystal form(s) or polymorph(s) of (6R)-5,10-CH$_2$-THF or its hemisulfate salt, preferably amounts of greater than 50%, 60%, 70%, 80%, 90% or 95% of one (or more) crystal form(s) or polymorph(s) of (6R)-5,10-CH$_2$-THF or its hemisulfate salt. The amount, degree and nature of the crystallinity of the crystalline compound of (6R)-5,10-CH$_2$-THF or its hemisulfate salt may be determined by one or more technical means including optical microscopy, electron microscopy, X-ray powder diffraction, solid state NMR spectroscopy or polarizing microscopy.

As used herein, "hemisulfate salt of 5,10-methylene-(6R)-tetrahydrofolic acid" means all crystalline and amorphous forms thereof, including dissolved salts, lyophilized forms of dissolved salts, and reconstituted lyophilized forms, including forms prepared by lyophilizing neutral to slightly acidic or basic solutions of the dissolved salt.

The term "crystalline purity," as used herein, means percentage of a particular crystalline form of a compound in a sample, which may contain the amorphous form of the compound, one or more other crystalline forms of the compound (other than the particular crystalline form of the compound), or a mixture thereof. The term "substantially crystalline form", as used herein, refers to at least about 80%, preferably at least about 90%, preferably at least about 95% crystalline purity, preferably about 97% crystalline purity, more preferably about 99% or more crystalline purity, and most preferably about 100% crystalline purity. Crystalline purity is determined by X-ray powder diffraction (XRPD), Infrared Raman spectroscopy and other solid state methods.

The term "chemical purity," as used herein, means percentage of a particular compound in a sample. The term "substantial chemical purity", as used herein, refers to a compound in about 80% chemical purity, preferably about 90%, more preferably about 95%, more preferably about 97%, more preferably about 98% chemical purity, and most preferably 99% or higher than 99%, e.g., 99.5, 99.6, 99.7, 99.8, 99.9 or up to 100% chemical purity, as determined by HPLC. Chemical impurities may include unreacted starting material (including solvents), degradation products of (6R)-5,10-$CH_2$-THF (such as tetrahydrofolic acid and its degradation products), etc.

As indicated above, the crystalline form of the hemisulfate salt of (6R)-5,10-$CH_2$-THF (and its purity) may be identified, characterized and distinguished from other salt forms, such as other sulfate salt forms, by unique solid state signatures with respect to, for example, X-ray powder diffraction (XRPD), Infrared Raman spectroscopy and other solid state methods, as shown by the data provided herein.

In one embodiment, the hemisulfate salt of (6R)-5,10-$CH_2$-THF includes in all its specific embodiments particular molar ratios between (6R)-5,10-$CH_2$-THF and sulfuric acid, i.e., 2:1 or some amount close to such ratio, e.g., 1.6-2.4:1, 1.8-2.2:1, or 1.9-2.1:1, 1.96-2.04:1, 1.98-2.02:1 or 1.99-2.01:1. In another embodiment, the hemisulfate salt of (6R)-5,10-$CH_2$-THF is preferably provided in chemically and/or (stereo)isomerically and/or crystalline pure form. In one specific embodiment it is in substantially crystalline form.

In another embodiment, the sulfate salt of (6R)-5,10-$CH_2$-THF includes in all its specific embodiments particular molar ratios between (6R)-5,10-$CH_2$-THF and sulfuric acid, i.e., 1:1 or some amount close to such ratio, e.g., 0.8-1.2:1, 0.9-1.1:1, or 0.985-1.05:1, 0.98-1.02:1, 0.99-1.01:1 or 0.995-1.005:1. In another embodiment, the sulfate salt of (6R)-5,10-$CH_2$-THF is preferably provided in chemically and/or (stereo)isomerically and/or crystalline pure form. In one specific embodiment it is in substantially crystalline form.

One specific embodiment is a crystalline form of the anhydrous hemisulfate salt of (6R)-5,10-$CH_2$-THF (hereinafter also called crystalline form Type 1), characterised in that it provides:
(i) an X-ray powder diffraction (XRPD) pattern which gives calculated lattice spacings (expressed in 2θ±0.2° 2θ (CuKα radiation)) at 4.7°, 17.9°, and 23.3°, preferably 4.7°, 16.6°, 17.9°, 18.4°, 18.9°, 20.2°, 23.3°, 23.5°, 24.3° and 24.7°; and/or
(ii) an FT-Raman spectrum containing peaks at wavenumbers (expressed in ±2 $cm^{-1}$) of 1672, 1656, 1603, 1553, 1474, 1301, 637, 624 and 363 and/or
(iii) an IR-spectrum having one or more absorption bands according to Table 3.

In preferred embodiments the hemisulfate salt of (6R)-5,10-$CH_2$-THF is characterized by at least 2 of the following 10 XRPD peaks (expressed in 2θ±0.2° 2θ (CuKα radiation)) at 4.7°, 16.6°, 17.9°, 18.4°, 18.9°, 20.2°, 23.3°, 24.3° and 24.7°, preferably 4.7°, 17.9°, and 23.3° and at least 2 of the following 9 FT-Raman peaks (expressed in ±2 $cm^{-1}$) of 1672, 1656, 1603, 1553, 1474, 1301, 637, 624 and 363.

In other preferred embodiments, the hemisulfate salt of (6R)-5,10-$CH_2$-THF provides an FT-Raman spectrum substantially in accordance with FIG. 1 and/or peaks as reported in Table 1 and/or an X-ray powder diffraction (XRPD) pattern substantially in accordance with FIG. 2(a) and/or peaks as reported in Table 2.

TABLE 1

Raman peak table (vs = very strong, s = strong, m = medium, w = weak, vw = very weak intensity).

| Wavenumber [$cm^{-1}$] | Intensity (qualitative) |
| --- | --- |
| 3019 | w |
| 2933 | m |
| 2880 | m |
| 1672 | s |
| 1656 | s |
| 1603 | vs |
| 1553 | m |
| 1474 | m |
| 1373 | m |
| 1337 | m |
| 1301 | s |
| 1207 | m |
| 1127 | w |
| 975 | m |
| 884 | m |
| 815 | w |
| 700 | w |
| 665 | w |
| 637 | s |
| 624 | s |
| 363 | m |

TABLE 2

Powder X-ray diffraction peak table expressed in 2θ ± 0.2° 2θ (CuKα radiation) (vs = very strong, s = strong, m = medium, w = weak, vw = very weak intensity).

| Angle in 2θ° | d-spacings in Å | Intensity (qualitative) |
| --- | --- | --- |
| 4.7 | 18.8 | vs |
| 9.4 | 9.4 | vw |
| 11.6 | 7.6 | w |
| 11.8 | 7.5 | w |
| 12.5 | 7.1 | vw |
| 13.6 | 6.5 | vw |
| 14.2 | 6.2 | m |
| 16.6 | 5.35 | s |
| 16.8 | 5.28 | m |
| 17.9 | 4.96 | vs |
| 18.4 | 4.83 | s |
| 18.9 | 4.68 | s |
| 20.2 | 4.38 | s |
| 21.0 | 4.23 | w |
| 21.7 | 4.09 | w |
| 23.3 | 3.82 | vs |
| 23.5 | 3.78 | s |
| 24.0 | 3.70 | m |
| 24.3 | 3.66 | s |
| 24.7 | 3.60 | m |
| 25.1 | 3.54 | m |
| 26.2 | 3.40 | m |
| 26.5 | 3.36 | m |
| 27.0 | 3.30 | m |
| 28.0 | 3.18 | w |
| 29.2 | 3.05 | m |
| 30.4 | 2.94 | w |

TABLE 2-continued

Powder X-ray diffraction peak table expressed in 2θ ± 0.2° 2θ
(CuKα radiation) (vs = very strong, s = strong, m = medium,
w = weak, vw = very weak intensity).

| Angle in 2θ° | d-spacings in Å | Intensity (qualitative) |
|---|---|---|
| 31.0 | 2.88 | w |
| 31.7 | 2.82 | w |
| 35.5 | 2.53 | w |

The hemisulfate salt of (6R)-5,10-CH$_2$-THF is most efficiently characterized and distinguished from related compounds by the X-ray powder diffraction pattern as determined in accordance with procedures, which are known in the art (see e.g. J. Haleblian, J. Pharm. Sci. 64:1269, 1975; J. Haleblain and W. McCrone, J. Pharm. Sci. 58:911, 1969). FIG. 2(d), which shows an X-ray diffraction pattern of a hemisulfate salt of (6R)-5,10-CH$_2$-THF as prepared in the Examples in comparison with an X-ray diffraction pattern of the sulfate salt of (6R)-5,10-CH$_2$-THF, illustrates clearly the distinctive pattern of these two salts.

While it is known that the relative intensities of the peaks may vary, depending upon the sample preparation technique, the sample mounting procedure and the particular instrument employed, the compound of the hemisulfate salt of (6R)-5,10-CH$_2$-THF can be identified by distinct peaks and peak locations characteristic for the specific polymorph (with a minor variation in peak assignments of about ±0.5 degrees 2theta (2θ), preferably ±0.2 degrees 2theta (2θ) (CuKα radiation).

In one embodiment, the hemisulfate salt of (6R)-5,10-CH$_2$-THF is in unsolvated anhydrous form, which includes compounds that are fully free of water and compounds which may contain traces of water. Such possible residual (not stoichiometric) water content may be any amount of water, but typically ranges from 0 wt.-% H$_2$O to 3 wt.-% H$_2$O, preferably between 0 wt.-% H$_2$O and 1 wt.-% H$_2$O.

The hemisulfate compound can be stored in solid form, such as in form of a powder, lyophilisate, or as a liquid.

In a specific embodiment, the hemisulfate salt of (6R)-5,10-CH$_2$-THF are prepared by adding an aqueous formaldehyde solution of (6S)-tetrahydrofolic acid to an aqueous solution of sulfuric acid (or an aqueous solution of acetic acid and sulfuric acid) and allowing crystallization of the hemisulfate salt of (6R)-5,10-CH$_2$-THF to occur. This crystallization reaction is performed at elevated temperatures, e.g. at a temperature of more than 35° C. In particular, the methods of preparation of the crystalline hemisulfate salt of (6R)-5,10-CH$_2$-THF comprise the steps of (i) reacting a solution of (6S)-tetrahydrofolic acid with an aqueous formaldehyde solution to obtain (6R)-5,10-CH$_2$-THF in solution (according to known procedures), (ii) adding the obtained (6R)-5,10-CH$_2$-THF in solution into an aqueous solution of sulfuric acid (or alternatively into an aqueous solution of acetic acid and sulfuric acid) at a temperature of more than 35° C., preferably between 35° C. and 70° C., more preferably between 40° C. and 60° C., most preferably 40° C. and 50° C. to allow crystallization of the hemisulfate of (6R)-5,10-CH$_2$-THF to occur, and (iii) isolating the obtained crystalline hemisulfate salt of (6R)-5,10-CH$_2$-THF by e.g. filtration.

Step (i) may be carried out according to known procedures as described in the Examples.

In step (ii) the obtained clear solution may be added to a sulfuric acid solution (or an aqueous solution of acetic acid and sulfuric acid) at a temperature of about 40 to 50° C., allowing the selective crystallization of the desired product. Optionally, after addition is completed, the obtained reaction mixture may be stirred at a temperature of about 40 to 50° C., for up to 5 hours, subsequently the crystallized product is then filtered off or centrifuged at the same temperature, optionally washed with water, and dried.

In one embodiment, the hemisulfate salt of (6R)-5,10-CH$_2$-THF is milled or micronized to a homogeneous consistency, for example, to a powder. Such powder form preferably facilitates the dissolution of the hemisulfate salt of (6R)-5,10-CH$_2$-THF, i.e. increases the dissolution rate.

One embodiment is directed towards a pharmaceutical composition comprising (a therapeutically effective amount of) the hemisulfate salt of (6R)-5,10-CH$_2$-THF and a pharmaceutically acceptable carrier for administration to a patient. The term "pharmaceutically acceptable" as used herein indicates that the carrier is approved or recognized for use in animals, and more particularly in humans, i.e. it is not toxic to the host or patient. In addition, a carrier of choice will not interfere with the effectiveness of the biological activity of the active ingredient. The term "carrier" refers to any auxiliary material necessary for the particular mode of administration of choice and includes e.g. solvents (diluents) excipients, or other additives with which the hemisulfate salt of (6R)-5,10-CH$_2$-THF is administered. Typically used diluents pharmaceutical carriers include sterile liquids, such as aqueous solutions and oils (e.g. of petroleum, animal, vegetable or synthetic origin), e.g. peanut oil, soybean oil, mineral oil, sesame oil and the like. Typically used aqueous liquids include water, saline solutions, aqueous dextrose and glycerol solutions and the like. Suitable pharmaceutical excipients include citric acid, ascorbic acid, starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Optionally the composition may comprise additives, such as wetting or emulsifying agents, pH buffering agents or binders. Examples of suitable pharmaceutical carriers are well known in the art and are described in e.g. "Remington's Pharmaceutical Sciences" by E. W. Martin (18th ed., Mack Publishing Co., Easton, Pa. (1990).

Optionally, a pharmaceutical composition of the hemisulfate salt of (6R)-5,10-CH$_2$-THF may further comprise at least one additional therapeutic agent. In specific embodiments the at least one additional therapeutic agent may be selected from bactericides, antibiotics, antivirals, antiseptics, antineoplastics, anticancer compounds such as chemotherapeutic agents, antifungals, and/or anti-inflammatory agents or other bioactive or therapeutic agents that are suitable for human use, in particular anticancer compounds such as chemotherapeutic agents. An anticancer drug such as a chemotherapeutic agent, may include but is not limited to chemotherapeutic agents that comprise specific binding members, proteins, nucleic acids or nucleic acid analogs (such as, but not limited to antisense molecules, ribozymes, and siRNAs), lipids, steroids, large molecules, small molecules, or metals. The one or more anticancer drugs can comprise one or more chemotherapeutic agents, such as but not limited to: nucleic acids, in particular fluorinated nucleic acids (e.g. 5-flurouracil or an analog or prodrug thereof), antifolates (e.g. pemetrexed, raltitrexed, lometrexol), topoisomerase inhibitors (e.g. irinotecan, topotecan), antimetabolite drugs (e.g. methotrexate, gemcitabine, tezacitabine), 5-FU modulators, alkylating agents (e.g. cyclophosphamide, carmustine), nucleic acid biosynthesis inhibitors (such as mitomycin, anthracyclines (e.g. epirubicin, doxorubicin), platinum derivatives (e.g. cisplatin, oxaliplatin, carboplatin), microtubule disrupting drugs (e.g. paclitaxel, docetaxel, vinolrebine, vincristine), hormone blocking drugs (e.g. tamoxifen), inhibitors of kinases, including but not limited to receptor and nonreceptor tyrosine kinases (e.g. Iressa, Tarceva, SU5416, PTK787, Gleevec), proteosome inhibitors (e.g. bortezomib), immune modulators (e.g. levamisole), anti-inflammatory drugs, vascularization inhibitors, cytokines (e.g. interleukins, tumor necrosis factors), and drugs that inhibit the activity of cytokines, hormones, or receptors for cytokines or hormones (e.g. the anti-VEGF antibody bevacizumab or "Avastin"). Anticancer drugs may also include monoclonal antibodies, such as but not limited to monoclonal antibodies that bind cytokines, hormones, or hormone receptors (e.g. antibodies that block activation of EGF or VEGF growth factors, such as Avastin, Erbitux, herceptin), etc.

In further aspects, both the sulfate and the hemisulfate salt of (6R)-5,10-CH$_2$-THF or lyophilisates prepared from said compounds, as well as reconstituted solution forms from said lyophilisates, are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors.

Additionally, the hemisulfate salt of (6R)-5,10-CH$_2$-THF or a lyophilisate prepared from the sulfate or the hemisulfate salt of (6R)-5,10-CH$_2$-THF, as well as a reconstituted solution form from said lyophilisates are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethyl-propanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[di-amineplatinum(II)]bis[diamine-(chloro)platinum(II)] tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methyl-sulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylene-dioxy)-5-methyl-7-hydroxy-8-methoxy-benzo[c]phenanthridinium, 6,9-bis[(2-aminoethyl)-amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethyl-amino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)-sulfonyl]-N'-(3,4-dichlorophenyl)urea, N6-[4-deoxy-4-[N2-[2(E),4(E)-tetradecadienoyl]-glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0) tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

The medicaments of the following table are preferably, but not exclusively, combined with the hemisulfate salt of (6R)-5,10-$CH_2$-THF or a lyophilisate prepared from the sulfate or the hemisulfate salt of (6R)-5,10-$CH_2$-THF, as well as a reconstituted solution form from said lyophilisates.

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffrnann-La Roche) |
| | Ormiplatin | |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | |
| | | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothec | |
| | Topotecan | TAS-103 (Taiho) |
| | Dexrazoxanet (TopoTarget) | Elsamitrucin (Spectrum) |
| | Pixantrone (Novuspharrna) | J-107088 (Merck & Co) |
| | Rebeccamycin analogue (Exelixis) | BNP-1350 (BioNumerik) |
| | | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |

-continued

| | | |
|---|---|---|
| | Cryptophycin 52 (Eli Lilly) | AVLB (Prescient |
| | Vinflunine (Fabre) | NeuroPharma) |
| | Auristatin PE (Teikoku Hormone) | Azaepothilon B (BMS) |
| | | BNP-7787 (BioNumerik) |
| | BMS 247550 (BMS) | CA-4-prodrug (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | lonafarnib (Schering-Plough) | |
| | BAY-43-9006 (Bayer) | Perillyl alcohol (DOR BioPharma) |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyltransferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | | BMS-275291 (Celltech) |
| Ribonucleoside reductase inhibitors | Marimastat (British Biotech) | Tezacitabine (Aventis) |
| | Gallium maltolate (Titan) | Didox (Molecules for Health) |
| | Triapin (Vion) | |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | | !3-Alethin (Dovetail) |
| | Melanoma vaccine (CTL Immuno) | CLL-Thera (Vasogen) |
| | p21-RAS vaccine (GemVax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | Medroxyprogesterone | Leuporelin |
| | Testosterone | Bicalutamide |
| | Testosterone propionate | Flutamide |
| | Fluoxymesterone | Octreotide |
| | Methyltestosterone | Nilutamide |
| | Diethylstilbestrol | Mitotan |
| | Megestrol | P-04 (Novogen) |
| | Tamoxifen | 2-Methoxyoestradiol (EntreMed) |
| | Toremofin | |
| | Dexamethasone | Arzoxifen (Eli Lilly) |

| | | |
|---|---|---|
| Photodynamic agents | Talaporfin (Light Sciences)<br>Theralux (Theratechnologies)<br>Motexafin-Gadolinium (Pharmacyclics) | Pd-bacteriopheophorbide (Yeda)<br>Lutetium-Texaphyrin (Pharmacyclics)<br>Hypericin |
| Tyrosine kinase inhibitors | Imatinib (Novartis)<br>Leflunomide (Sugen/Pharmacia)<br>ZD1839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, AIIos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor Ribapharm)<br>Cilengitide (integrin antagonist, Merck KGaA)<br>SR-31747 (IL-1 antagonist, Sanofi-Synthelabo)<br>CCI-779 (mTOR kinase inhibitor, Wyeth)<br>Exisulind (PDE-V inhibitor, Cell Pathways)<br>CP-461 (PDE-V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>Bortezomib (proteasome inhibitor, Millennium)<br>SRL-172 (T-cell stimulant, SR Pharma)<br>TLK-286 (glutathione-S transferase inhibitor, Telik)<br>PT-100 (growth factor agonist, Point Therapeutics)<br>Midostaurin (PKC inhibitor, Novartis)<br>Bryostatin-1 (PKC stimulant, GPC Biotech) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidine (PPT inhibitor, PharmaMar)<br>Rituximab (CD20 antibody, Genentech)<br>Gemtuzumab (CD33 antibody, Wyeth Ayerst)<br>PG2 (haematopoiesis promoter, Pharmagenesis)<br>Immunol ™ (triclosan mouthwash, Endo)<br>Triacetyluridine (uridine prodrug, Wellstat)<br>SN-4071 (sarcoma agent, Signature BioScience)<br>TransMID-107 ™ (immunotoxin, KS Biomedix)<br>PCK-3145 (apoptosis promoter, Procyon)<br>Doranidazole (apoptosis promoter, Pola)<br>CHS-828 (cytotoxic agent, Leo)<br>trans-Retinic acid (differentiator, NIH)<br>MX6 (apoptosis promoter, MAXIA)<br>Apomine (apoptosis promoter, ILEX Oncology)<br>Urocidine (apoptosis promoter, Bioniche) |

| | |
|---|---|
| CDA-II (apoptosis promoter, Everlife) | Ro-31-7453 (apoptosis promoter, La Roche) |
| SDX-101 (apoptosis promoter, Salmedix) | Brostallicin (apoptosis promoter, Pharmacia) |
| Ceflatonin (apoptosis promoter, ChemGenex) | |

The hemisulfate salt of (6R)-5,10-CH$_2$-THF or pharmaceutical compositions thereof may be used for therapy, specifically in cancer chemotherapy, i.e. in a method for treatment of cancer, which comprises administering a therapeutically effective amount of a hemisulfate salt or pharmaceutical compositions thereof to a subject in need of such treatment. In another embodiment, the hemisulfate salt of (6R)-5,10-CH$_2$-THF (or pharmaceutical compositions thereof) is used in therapy, preferably in chemotherapy, i.e. in the treatment of cancer. Examples of cancers to be treated include, but are not limited to, breast cancer, esophageal cancer, gastric cancer, gall bladder cancer, bile duct cancer, colon cancer, rectal cancer, liver cancer, pancreatic cancer, ovarian cancer, head and neck cancer, and mesotheolioma cancer.

In a preferred embodiment the cancer is selected from various cancer forms including colon cancer, stomach cancer, breast cancer, bowel cancer, gallbladder cancer, lung cancer (specifically adenocarcinoma), colorectal cancer (CRC) including metastatic CRC, head and neck cancer, liver cancer and pancreatic cancer.

A suitable pharmaceutical composition may be adapted for oral, parenteral or rectal administration and, as such, may be in the form of tablets, capsules, oral liquid preparations, powders, lyophilisates, granules, lozenges, reconstitutable powders, injectable or infusable solutions or suspensions or suppositories. Preferably, the pharmaceutical compositions are in a form suitable for parenteral administration, such as intravenously or intramuscularly, subcutaneously, intra-arterially.

For parenteral administration, fluid unit dosage forms typically comprise reconstituted lyophilisates (of the hemisulfate salt or the sulfate salt), preferably of the hemisulfate salt of (6R)-5,10-CH$_2$-THF, optionally a further therapeutic agent, and a pharmaceutically acceptable carrier or diluent, to form e.g. water-based solutions or oil-based suspensions (or lyophilisates thereof). The compound, depending on the presence of other therapeutic agents, the carrier, and concentration used, may be either suspended or dissolved in a carrier. For parenteral solutions, the compound may be dissolved for injection and filter sterilised before filling into a suitable vial or ampoule and sealing. Optionally, adjuvants such as a local anaesthetic, preservatives and buffering agents are dissolved in the vehicle. If desired, the obtained solutions may be subjected to lyophilization (i.e. the composition may be frozen after filling into the vial and the water removed under vacuum). For parenteral suspensions, the compound is suspended in the vehicle (instead of being dissolved) and preferred sterilization includes exposure to ethylene oxide before suspension in a sterile vehicle (such as a vial or ampoule). Optionally, a surfactant or wetting agent may be included in the composition to facilitate uniform distribution of the compound.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

In case of a combination therapy wherein a pharmaceutical composition comprises a hemisulfate salt of (6R)-5,10-CH$_2$-THF and at least one further therapeutic agent, the active agents may be administered as part of the same pharmaceutical composition or the at least one further therapeutic agent may be administered separately, i.e. as a separate (and possibly different) pharmaceutical compositions, optionally via different administration routes, either simultaneously or sequentially.

The dose of the active agent(s), i.e. hemisulfate salt of (6R)-5,10-CH$_2$-THF (and optionally the at least one further therapeutic agent), used in a treatment as described herein, will depend on various factors, including age and health condition of the subject to be treated, type and severity of the disease to be treated, route and frequency of administration, and the like. Those skilled in the art of cancer treatment and chemotherapy would be able to determine therapeutically effective amounts and regimens for the hemisulfate salt of (6R)-5,10-CH$_2$-THF alone or in combination with at least one further therapeutic agent as defined above, based on known protocols for evaluating toxicity and efficacy.

The term "therapeutically effective amount" refers to the amount of active compound that elicits the biological or medicinal response in a tissue, system, animal, individual or human that is being sought by a skilled practitioner (e.g. researcher, veterinarian, medical doctor or other clinician or caregiver), which includes (i) prevention of the disease; and/or (ii) inhibition of the disease (e.g. arresting further development of the pathology and/or symptomatology); and/or (iii) amelioration of the disease (e.g. reversing the pathology and/or symptomatology) Likewise the term "treatment" as used herein refers to (i) prevention of the disease; and/or (ii) inhibition of the disease (e.g. arresting further development of the pathology and/or symptomatology); and/or (iii) amelioration of the disease (e.g. reversing the pathology and/or symptomatology).

A pharmaceutical composition of choice may contain from 0.1% to 99 wt %, preferably from 10 to 60 wt %, of the active agent (i.e. the hemisulfate salt of (6R)-5,10-CH$_2$-THF or a lyophilisate prepared from the sulfate or the hemisulfate salt of (6R)-5,10-CH$_2$-THF optionally in combination with at least one further therapeutic agent), depending on the method of administration.

Typical dosage ranges of the hemisulfate salt of (6R)-5, 10-CH$_2$-THF or a lyophilisate prepared from the sulfate or the hemisulfate salt of (6R)-5,10-CH$_2$-THF to be used in cancer treatment may range from 5 mg/m$^2$ to 1.5 g/m$^2$, preferably from 30 mg/m$^2$ to 500 mg/m$^2$ (for colorectal cancer treatment) resp. 10 mg/m$^2$ to 1000 mg/m$^2$ (for Methotrexate therapy), and more preferably from about 60 mg/m$^2$ to about 300 mg/m$^2$ (for colorectal cancer treatment) resp. 50 mg/m$^2$ to 500 mg/m$^2$ (for Methotrexate therapy).

The following Examples serve as illustrations of the present disclosure without intending to limit its scope.

FIRST SET OF EXAMPLES

Differential Scanning calorimetry (Thermal Analysis Q2000): Closed (hermetically sealed) gold crucibles; sample filled under ambient conditions or after 3 minutes of equilibration in an N$_2$ environment; heating rate of 10 K min-1; −50° C. to 254° C. range. When two heating scans were carried out, the sample was rapidly cooled to −50° C. between the scans. Listed transition temperatures correspond to peak maxima and minima, not to onset temperatures.

FT-Raman Spectroscopy (Bruker RFS100; with OPUS 6.5 software; offline data analysis carried out with OPUS 7.0 software): Nd:YAG 1064-nm excitation; 300 mW nominal laser power; Ge detector; 64-256 scans; 3500-100 cm$^{-1}$ spectral range used for analysis; 2 cm$^{-1}$ resolution.

$^1$H-NMR (Bruker DPX300): $^1$H-NMR spectra were recorded using a proton frequency of 300.13 MHz, a 30° excitation pulse, and a recycle delay of 1 s. Either 16 or 256 scans were accumulated, and deuterated DMSO was used as the solvent. The solvent peak was used for referencing, and chemical shifts are reported on the TMS scale.

$^{13}$C NMR (Bruker AMX 300): The $^{13}$C NMR spectrum was obtained using a Bruker AMX 300 spectrometer equipped with a 5 mm TXO probehead. The hemisulfate was dissolved in 0.1N NaOD. The spectrum was measured at 303 K, with 4000 scans and a digital resolution of 32768 data points. Chemical shifts are given in ppm relative to internal TSP (((3-trimethylsilyl)-2,2',3,3'-tetradeuteropropionic acid, sodium salt)) standard.

Powder X-Ray Diffraction (Bruker D8 Advance): Copper Kα radiation, 40 kV/40 mA, LynxEye detector, Bragg-Brentano reflection geometry, 0.02° 2θ step size, 37 s step time, 2.5-50° 2θ range. Powder samples were measured in 0.1-mm or 0.5-mm deep silicon single-crystal sample holders. No special treatment was used in preparing the samples other than the application of slight pressure to get a flat surface. An ambient air atmosphere was used for all measurements, and the samples were rotated during the measurement. Absent any information to the contrary X-Ray Diffraction data is shown as reflection data.

Powder X-Ray Diffraction (Stoe Stadi P.): Copper Kα1 radiation, 40 kV/40 mA, Mythen1K detector, transmission mode, curved Ge monochromator, 0.02° 2θ step size, 60 s step time, 1.5-50.5° 2θ scanning range with 1° 2θ detector step in step-scan mode. The samples (10-20 mg of powder) were measured between two acetate foils. No special treatment was used in preparing the samples. An ambient air atmosphere was used for all measurements, and each sample was rotated during the measurement.

TG-FTIR (Netzsch Thermo-Microbalance TG 209 with Bruker FT-IR Spectrometer IFS 28): Al crucible (with microhole); N$_2$ atmosphere; 10 K min$^{-1}$ heating rate; 25° C. to 300° C. range.

IR (FT-IR Paragon 1000): The infrared spectrum was recorded in 100 scans on a Perkin Elmer Fourier Transform Infrared System from a hemisulfate sample pressed in a bromide disk.

Example 1-1: Preparation of (6R)-5,10-CH$_2$-THF Hemisulfate Salt

A solution of (6S)-tetrahydrofolic acid (16 mmol, 7.93 g) in 78.0 g distilled water was provided in a roundbottom flask at room temperature under N$_2$. The pH of this solution was adjusted to pH 11 by adding (slowly) a 32% NaOH solution. As soon as the solution became clear, a 1.00M HCl solution was added to adjust the pH of the solution to 8.3 at 25° C. The obtained clear solution was cooled to about 0° C., at which temperature it showed a pH of 8.8. By addition of 1M HCl the pH was adjusted to pH=8.6 and 1.44 g of a 36.8% HCHO solution (110 mol %) were added in one portion. Upon completion of the addition the solution was stirred at 0° C. (ice bath) for 1 hour. Active charcoal (0.2 g, Norit C Extra) was added and the reaction mixture was stirred for 30 minutes at 0° C. and then cold filtered over a suction filter to obtain a clear solution, which was used in step (b) without further purification.

(b) A mixture of 55 ml 1M H$_2$SO$_4$ and 55 ml glacial acetic acid was provided in a roundbottom flask at 60° C. under N$_2$. To this solution was added dropwise over a time period of 15 minutes the solution as obtained in step (a) and the obtained reaction mixture was stirred at 50° C. for 2 hours. The reaction mixture was then filtered at 50° C. over a suction filter, washed twice with 25 ml distilled water at room temperature and dried at 30° C. and 10 mbar for 12 hours (overnight) to obtain the (6R)-5,10-CH$_2$-THF hemisulfate salt in form of light gray crystals (7.36 g, 86% yield). The obtained product had a purity of 98.4% as determined by HPLC, and an isomeric purity of 97.6% (6R-isomer). Analysis by XRPD showed the crystal form Type 1 (for complete characterization see Examples 2 and 3).

Example 1-2: Characterization (a) The FT Raman spectrum of (6R)-5,10-CH$_2$-THF hemisulfate salt, recorded using a nominal laser power level of 300 mW and 64 scans is shown in FIG. 1.
(b) The corresponding powder X-ray diffractogram, recorded in transmission mode, is shown in FIG. 2(*b*).
(c) The TG-FTIR thermogram of (6R)-5,10-CH$_2$-THF hemisulfate salt is shown in FIG. 3. It was carried out under N$_2$ flow (to avoid oxidative degradation). The sample shows a loss of 0.5 wt % H$_2$O from ca. 40° C. to 210° C., which is residual water (due to either hygroscopicity or incomplete drying). Decomposition occurs only above 210° C.
(d) The DSC thermogram of (6R)-5,10-CH$_2$-THF hemisulfate salt is shown in FIG. 4. Prior to the first heating scan, the sample was equilibrated for three minutes under gaseous nitrogen flow and lost 0.6 wt.-% of its mass during that time. This is consistent with the water content observed in the TG-FTIR thermogram (see FIG. 3) and confirms that this water is loosely bound. The sample was subsequently heated in a closed gold crucible to 254° C. at 10 K min$^{-1}$, quench cooled to −50° C., and heated a second time at 10 K min$^{-1}$. The only thermal event in the first heating scan is an endothermal at approximately 247.4° C. (ΔH≈60.9 J g$^{-1}$), which is attributable to melting. This endothermal event possibly overlaps with the onset of an exothermic degradation. In the second heating scan, a glass transition is observable at $T_g \approx 104°$ C. ($\Delta C_p = 0.38$ J $g^{-1}K^{-1}$), which confirms that melting occurred in the first scan. No other thermal events were observed up to 250° C.

(e) The IR spectrum was recorded in a pressed KBr pellet and the characteristic absorption bands are shown in Table 3.

TABLE 3

IR-spectrum of the hemisulfate salt of (6R)-5,10-CH$_2$-THF (Type 1) with absorption bands in cm$^{-1}$ and their assignment

| Absorption band (cm$^{-1}$) | Assignment |
| --- | --- |
| 3346 | OH and NH stretch |
| 3168 | OH of intramolecular hydrogen bridges, CH$_2$ stretch |
| 1709, 1654 | CO-stretching vibration of monosubstituted amide |
| 1612 | Symmetrical and antisymmetrical stretching vibration of COO$^-$ |
| 1560, 1504 | Aryl and pyrimidine ring stretch |
| 1397, 1300 | Symmetrical and antisymmetrical stretching vibration of COO$^-$ |
| 824 | Aryl adjacent hydrogen wag of para substituted aromatic |

(f) The $^1$H NMR spectrum of (6R)-5,10-CH$_2$-THF hemisulfate salt was recorded in DMSO-d$_6$ and the chemical shifts (d) in ppm are shown in Table 8.

TABLE 8

$^1$H-NMR of the hemisulfate salt of (6R)-5,10-CH$_2$-THF with chemical shifts (d) in ppm (d = doublet, m = multiplet, t = triplet; with TSP at 0 ppm and solvent D$_2$O/NaOD 4.85 ppm)

| δ (1H) | Multiplicity | Intensity |
| --- | --- | --- |
| 7.75 | d | 2H |
| 6.62 | d | 2H |
| 4.99 | m | 1H |
| 4.33 | m | 1H |
| 3.74 | m | 2H |
| 3.52 | m | 1H |
| 3.28 | m | 2H |
| 2.91 | m | 1H |
| 2.33 | t | 2H |
| 2.17 | m | 1H |
| 2.05 | m | 1H |

(g) The $^{13}$C NMR was recorded in 0.1N NaOD and the chemical shifts (d) in ppm relative to TSP are shown in Table 9.

TABLE 9

$^{13}$C-NMR of the hemisulfate salt of (6R)-5,10-CH$_2$-THF with chemical shifts (d) in ppm (d = doublet, m = multiplet, t = triplet)

| δ (13C) | Multiplicity |
| --- | --- |
| 185.12 | s |
| 182.05 | s |
| 173.12 | s |
| 172.41 | s |
| 162.26 | s |
| 156.78 | s |
| 151.78 | s |
| 131.18 | d |
| 123.27 | s |
| 114.19 | d |
| 103.99 | s |
| 70.67 | t |
| 58.61 | d |

TABLE 9-continued $^{13}$C-NMR of the hemisulfate salt of (6R)-5,10-CH$_2$-THF with chemical shifts (d) in ppm (d = doublet, m = multiplet, t = triplet)

| δ (13C) | Multiplicity |
| --- | --- |
| 56.94 | d |
| 51.6 | t |
| 41.71 | t |
| 37.07 | t |
| 31.41 | t |

(h) Analysis of (6R)-5,10-CH$_2$-THF hemisulfate salt by optical microscopy confirmed its crystallinity. The sample consisted of agglomerates of small, birefringent particles.

Example 1-3: Stability Testing of (6R)-5,10-CH$_2$-THF Hemisulfate Salt (a) Suspension equilibration of (6R)-5,10-CH$_2$-THF hemisulfate salt as starting material at temperatures other than room temperature in a variety of solvents and mixture are summarized in Table 10:

TABLE 10

Suspension equilibration stability of (6R)-5,10-CH$_2$-THF hemisulfate salt

| Solvent(s) | Temperature (° C.) | Duration (h: hours; d: days) | Observation |
| --- | --- | --- | --- |
| MeOH/formic acid 1:1 | 50 | 2 h | No change |
| AcOH saturated with L-ascorbic acid | 50 | 1 d | No change |
| THF with ~2 mM L-ascorbic acid | 40 | 3 d | No change |
| 2-PrOH with ~2 mM L-ascorbic acid | 40 | 3 d | No change |
| PEG4500/EtOH 1:9 saturated with L-ascorbic acid | 50 | 7 d | No change |
| H$_2$O | 5 | 6 d | No change |
| formic acid/THF 1:3 | 10-20 | 6 d | No change |
| AcOH saturated with L-ascorbic acid | 50 | 5 d | No change |
| MeCN saturated with L-ascorbic acid | 50 | 5 d | No change |

(b) Stability in 85% ethanol at room temperature (6R)-5,10-CH$_2$-THF hemisulfate salt (3.01 g) was dispersed in 100 ml 85% EtOH at room temperature and stirred for 5 h, then filtered and dried at 30° C. and 8 mbar for 12 hours (over night). Analysis by XRPD showed that the X-ray pattern distinctive for the crystal form Type 1 remained unchanged.

(c) Stability at high temperature/low pressure (6R)-5,10-CH$_2$-THF hemisulfate salt (2.17 g) was placed in a drying chamber at 65° C. and 8 mbar for 21 h. Analysis by XRPD showed that the X-ray pattern distinctive for the crystal form Type 1 remained unchanged.

(d) Long-term stability of (6R)-5,10-CH$_2$-THF hemisulfate salt and pharmaceutical composition thereof In order to determine the long-term stabilities of (6R)-5,10-CH$_2$-THF hemisulfate salt, the salts were stored in air at 25° C. and at 60% relative humidity. The content of (6R)-5,10-CH$_2$-THF hemisulfate salt remaining was measured by HPLC at periodic intervals and is given by comparison with the initial value (% rel.). The results are shown in Table 11.

TABLE 11

Long-term stability of three different production
batches of (6R)-5,10-CH$_2$-THF hemisulfate salt (6R)-5,10-CH$_2$-THF hemisulfate (% rel.)

| | 0 months | 3 months | 6 months | 9 months | 12 months | 18 months | 24 months | 36 months |
|---|---|---|---|---|---|---|---|---|
| (6R)-5,10-CH$_2$-THF hemisulfate (batch 1) | 100.0 | 99.7 | 99.5 | 99.6 | 99.2 | 99.2 | 99.4 | 98.5 |
| (6R)-5,10-CH$_2$-THF hemisulfate (batch 2) | 100.0 | 99.9 | 99.9 | 100.0 | 99.7 | 99.4 | 99.4 | 99.0 |
| (6R)-5,10-CH$_2$-THF hemisulfate (batch 3) | 100.0 | 99.5 | 99.5 | 99.4 | 99.1 | 99.0 | 99.0 | |

Table 11 clearly is showing that (6R)-5,10-CH$_2$-THF hemisulfate is highly stable over a long period of time even at room temperature.

Example 1-4: Comparative Stability of (6R)-5,10-CH$_2$-THF Sulfate Salt

In order to compare the long-term stabilities of (6R)-5,10-CH$_2$-THF hemisulfate salt to the long-term stabilities of (6R)-5,10-CH$_2$-THF sulfate salt prepared according to EP 0 537 492 B1, stability data for (6R)-5,10-CH$_2$-THF sulfate salt has been generated at various temperatures and humidities.

(a) Stability of (6R)-5,10-CH$_2$-THF sulfate (6R)-5,10-CH$_2$-THF sulfate salt was prepared according to literature procedures (EP 0 537 492 B1) and stored for 15 months at −20° C. Subsequently, samples of the product were stored at 5° C. resp. at 25° C. and 60% relative humidity resp. at 40° C. and 75% relative humidity. The content of (6R)-5,10-CH$_2$-THF sulfate salt remaining in the sample was measured by HPLC at periodic intervals. The content of (6R)-5,10-CH$_2$-THF sulfate was compared to the initial value at the time of preparation (% rel.). The results are shown in Tables 13 and 14.

TABLE 13

Long-term stability of (6R)-5,10-CH$_2$-THF sulfate salt at −20° C.

| Temperature/relative humidity | (6R)-5,10-CH$_2$-THF sulfate (% rel.) | |
|---|---|---|
| | 0 months | 15 months |
| −20° C. | 100.0 | 98.7 |

TABLE 14

Subsequent long-term stability of (6R)-5,10-CH$_2$-THF sulfate salt at 5° C., 25° C./60% rh, resp. 40° C./75% rh

| Temperature/relative humidity | (6R)-5,10-CH$_2$-THF sulfate (% rel.) | |
|---|---|---|
| | 0 months | 6 months |
| 5° C. | 98.7 | 97.3 |
| 25° C./60% rh | 98.7 | 95.5 |
| 40° C./75% rh | 98.7 | 95.0 |

A comparison of the data in Tables 13 and 14 with the stability data of (6R)-5,10-CH$_2$-THF hemisulfate as disclosed in Example 1-3 clearly shows that i) there is a remarkable difference in stability of (6R)-5,10-CH$_2$-THF hemisulfate compared to (6R)-5,10-CH$_2$-THF sulfate and ii) (6R)-5,10-CH$_2$-THF hemisulfate is much more stable over a long period of time than (6R)-5,10-CH$_2$-THF sulfate.

(b) Content of the degradation product 10-formyl-(6R)-tetrahydrofolic acid (6R)-5,10-CH$_2$-THF sulfate salt was prepared according to literature procedures (EP 0 537 492 B1) and stored for 15 months at −20° C. Subsequently, samples of the product were stored at 5° C. resp. at 25° C. and 60% relative humidity resp. at 40° C. and 75% relative humidity. The content of 10-formyltetrahydrofolic acid, a major degradation product, was measured by HPLC at periodic intervals and disclosed as absolute values (% w/w). The results are shown in Tables 15 to 16.

TABLE 15

Content of the degradation product 10-formyltetrahydrofolic acid when stored at −20° C.

| Temperature/relative humidity | 10-formyltetrahydrofolic acid (% w/w) | |
|---|---|---|
| | 0 months | 15 months |
| −20° C. | 0.53 | 1.37 |

TABLE 16

Subsequent content of the degradation product 10-formyltetrahydrofolic acid when stored at 5° C., 25° C./60% rh, resp. 40° C./75% rh

| Temperature/relative humidity | 10-formyltetrahydrofolic acid (% w/w) | |
|---|---|---|
| | 0 months | 6 months |
| 5° C. | 1.37 | 1.47 |
| 25° C./60% rh | 1.37 | 1.89 |
| 40° C./75% rh | 1.37 | 2.36 |

The data in Tables 15 and 16 clearly show that over the observed storage time there is a remarkable increase of the degradation product 10-formyltetrahydrofolic acid. Such amounts of byproducts can not be seen with the hemisulfate salt of (6R)-5,10-CH2-THF stored under similar conditions (see e.g. Table 11).

Example 1-5: Pharmaceutical Dosage Forms of
(6R)-5,10-CH$_2$-THF Hemisulfate Salt (a) Lyophilisate for reconstitution to be used for intravenous application To 18.480 kg water at 4° C. where argon was sparged through for 1 hour 1.386 kg NaOH 2M and 968.9 g sodium citrate trihydrate was added. The mixture was stirred at 4° C. under argon up to a complete dissolution (pH 13.0). 473.9 g (6R)-5,10-CH$_2$-THF hemisulfate was then added under using 210 g of argon saturated rinse water of 4° C. (slow dissolution, pH 6.5). The pH was then set with NaOH 2M to 9.3±0.1 (121.8 g). 203.6 g of argon saturated water of 4° C. was added (total solution 21.844 kg).

The solution then was filtered through a sterile filter. Into each vial of 10 ml 5.201 g (5 ml) of the sterile filtrated solution was added and then lyophilized at −45° C.

Before injection 10 ml of water (WFI) was added to each vial (resulting in an osmolality of 293 mosmol/kg).

(b) Formulation of a lyophilized composition of (6R)-5,10-CH$_2$-THF hemisulfate at an essentially neutral pH The following materials (mg/100 ml) and procedure were used for obtaining the lyophilized composition:
Materials (mg/100 ml):
5.530 g (6R)-5,10-CH$_2$-THF hemisulfate salt (equivalent to 5.000 g (6R)-5,10-CH$_2$-THF)
6.000 g Citric acid, Anhydrous, Powder, USP
4.000 g Ascorbic acid, Granular, USP
NaOH/HCl to adjust pH
100 mg Water for Injection (WFI), USP to qs
(i) Procedure: Sparge WFI with filtered Nitrogen Gas, NF for 30 min.
(ii) Record tare wt of 100 ml plastic bottle.
(iii) Weigh out citric acid, ascorbic acid and about 90 g N$_2$ sparged water.
(iv) Mix to dissolve.
(v) Adjust pH to 7.0±0.1 with 1N NaOH or HCl.
(vi) Chill the solution to 10° C.
(vii) Add (6R)-5,10-CH$_2$-THF hemisulfate salt, mix to dissolve.
(viii) Record pH (7.0±0.2).
(ix) Add more water to 110 g final weight (or 100 ml). Record wt.
(x) Pass through a 0.2-micron filter while keeping the solution chilled as possible.
(xi) Fill into vials (2 ml or 100 mg 5,10-CH$_2$-THF per vial) while keeping the solution chilled as possible.
(xii) Freeze dry.
(xiii) Seal vials under slight vacuum with nitrogen in the headspace.
(xiv) Crimp the vials.

Example 1-6: Preclinical/Clinical Results (a) Results from pre-clinical investigations in animal models, performed according to the ICH S9 guidance, show that (6R)-5,10-CH$_2$-THF hemisulfate is safe at the highest dose-levels administered to rats (100 mg/kg/day) and dogs (50 mg/kg/day). Clinical data furthermore show that (6R)-5,10-CH$_2$-THF hemisulfate administered in doses of up to 200 mg/m$^2$ is safe for patients.
(b) In a single-blinded, randomized phase I/II study (ISO-CC-002) performed on 32 patients diagnosed with colon cancer the pharmacokinetic and pharmacodynamic properties of (6R)-5,10-CH$_2$-THF hemisulfate compared to Levoleucovorin in tumor tissue, adjacent mucosa and blood plasma were investigated. The study was performed at the Sahlgrenska University Hospital in Goteborg, Sweden. The analysis of the completed trial data showed that administration of (6R)-5,10-CH$_2$-THF hemisulfate gave substantially greater exposure and peak plasma concentrations of methylenetetrahydrofolate than those obtained after administration of Levoleucovorin. The concentrations of methylenetetrahydrofolate and tetrahydrofolate in both tumor and adjacent mucosa were also much higher after administration of (6R)-5,10-CH$_2$-THF hemisulfate than those obtained after administration of Levoleucovorin.

Another embodiment relates to stable pharmaceutical compositions of (6R)-5,10-CH$_2$-THF or the hemisulfate salt of (6R)-5,10-CH$_2$-THF in all aspects as described above. In this regard, any time the compound 5,10-methylene-(6R)-tetrahydrofolate is mentioned herein, it is considered to clearly include and/or be completely interchangeable with the hemisulfate salt, including in the second set of examples below.

In the present text, the term (6R)—CH$_2$-THF relates to 5,10-methylene-(6R)-tetrahydrofolic acid in the form of the free acids, in the form of pharmaceutically acceptable salts, particularly acidic salts, as well as alkali or alkaline earth metal salts. (6R)—CH$_2$-THF comprise both mixtures of optical isomers, particularly 1:1 mixtures of diastereoisomers, as well as optically pure diastereoisomers, particularly optically pure, natural 5,10-methylene-(6R)-tetrahydrofolic acid.

Pharmaceutically acceptable salts can be acidic salts, such as sulfate or sulfonate salts, preferably sulfate salts, even more preferably hemisulfate salts, or can also be alkali or alkaline earth metal salts, preferably sodium, potassium, magnesium or calcium salts.

(6R)—CH$_2$-THF is an active ingredient which is preferably used for parenteral administration in combination with fluorinated pyrimidines, such as 5-fluorouracil (5-FU), which is a widely used cytostatic agent for the treatment of solid tumours [Cofactor Biokeys Pharmaceuticals. Seley, K. L. Idrugs 4 (1), 99-101 (2001)]. (6R)—CH$_2$-THF is a reduced folate and achieves its chemotherapeutic effect together with the base analogue 5-FdUMP by inhibiting the enzyme thymidylate synthase (TS), which catalyses the conversion of deoxyuridylate (dUMP) to deoxythymidylate (dTMP), which is a central component of DNA synthesis. Since this step constitutes the only de novo source of deoxythymidylate in the cell, the inhibition of this key enzyme by pyrimidine bases such as 5-FU or the 5-FU prodrug capecitabine (Xeloda) is one of the main starting points in cancer therapy. Deactivation of TS occurs by the formation of a covalent, inhibiting ternary complex between TS, the base analogue 5-FdUMP, which is a metabolite of 5-FU, and (6R)—CH$_2$-THF. An enhancement of the cytotoxic effect of 5-FU can be achieved by increasing the intracellular concentration of (6R)—CH$_2$-THF, whereupon the stability of the ternary complex is increased. This causes direct inhibition of DNA synthesis and repair, which ultimately results in cell death and in the delaying of tumour growth.

The pharmaceutical use of (6R)—CH$_2$-THF is restricted by its extremely high sensitivity to oxidation by air [Chemical Stability and Human Plasma Pharmacokinetics of Reduced Folates. Odin, E. et al., Cancer Investigation 16 (7), 447-455 (1998). The structure of "Active Formaldehyde" (N$^5$N$^{10}$-methylene tetrahydrofolic acid), Osborn, M. J. et al., J. Am. Chem. Soc. 82, 4921-4927 (1960), Folates in Foods: Reactivity, stability during processing, and nutritional implications. Hawkes, J., and Villota, R. Food Sci. Nutr. 28, 439-538 (1989)]. 5,10-methylenetetrahydrofolic acid is an addition product of tetrahydrofolic acid and formaldehyde [5,10-methylene-5,6,7,8-tetrahydrofolate]. Conformation of the Tetrahydropyrazine and Imidazolidine Rings. Poe, M. et al. Biochemistry 18 (24), 5527-5530 (1979). Tetrahydrofolic Acid and Formaldehyde. Kallen, R. G. Methods in Enzymology 18B, 705-716 (1971)]. In aqueous solution there is an equilibrium between 5,10-methylenetetrahydrofolic acid on the one hand and tetrahydrofolic acid and formaldehyde on the other hand. The following procedures have hitherto been employed for the stabilization of solutions of 5,10-methylenetetrahydrofolates:

Rigorous exclusion of atmospheric oxygen by the use of special technical devices for the reconstitution of solid formulations and the injection of 5,10-methylenetetrahydrofolates in an air-free environment [Chemical Stability and Human Plasma Pharmacokinetics of Reduced Folates. Odin, E. et al., Cancer Investigation 16 (7), 447-455 (1998), Fluid Transfer Systems U.S. Pat. No. 4,564,054].

Addition of a reducing agent such as L(+)-ascorbic acid or salts thereof, reduced γ-glutathione, β-mercaptoethanol, thioglycerol, N-acetyl-L-cysteine, etc. as an antioxidant for the sensitive 5,10-methylenetetrahydrofolic acid and for tetrahydrofolic acid in particular.

Stabilization by means of cyclodextrin inclusion compounds: EP 0 579 996 (Eprova). Use of high concentrations of the active ingredient.

The following methods are also known for the stabilization of other tetrahydrofolic acid derivatives:

Stabilization of solutions containing 5-formyltetrahydrofolic acid by the addition of sodium citrate, sodium acetate or sodium chloride: EP 0 755 396 (Pharmachemie).

Stabilization of injection solutions containing a sodium or potassium salt of 5-formyltetrahydrofolic acid at a pH between 7.5 and 8.5: EP 0 677 159 (SAPEC).

Stabilization of solutions containing the calcium salt of 5-formyltetrahydrofolic acid by the addition of sodium citrate: U.S. Pat. No. 4,931,441 (Luitpold Pharmaceutical).

However, the stabilization of 5-formyltetrahydrofolic acid, particularly solutions thereof, cannot be compared with the stabilization of (6R)—$CH_2$-THF solutions. Thus the methylene group in (6R)—$CH_2$-THF, which is incorporated in a five-membered ring, results in properties of this substance which differ considerably from those of 5-formyltetrahydrofolic acid. This is manifested, for example, in significantly different stability behaviour and in different paths of decomposition. In contrast to 5-formyltetrahydrofolic acid, 5,10-methylenetetrahydrofolic acid in solution is always in equilibrium with formaldehyde and tetrahydrofolic acid, which is distinguished by its extremely high sensitivity to oxidation. In contrast, 5-formyltetrahydrofolic acid does not exhibit this dissociation behaviour and is generally very stable in pharmaceutically acceptable aqueous solutions, even without the addition of sodium citrate and sodium hydroxide.

It has been found that the stability of (6R)—$CH_2$-THF in aqueous solutions, in suspensions and in solid forms such as powders or lyophilisates can be strikingly increased by adjusting to a slightly acidic to basic pH, with the simultaneous use of citrate. This stabilization occurs even in the absence of a reducing agent. Likewise, the same approach is applicable to the stabilization of the hemisulfate respectively the sulfate salt of (6R)-5,10-$CH_2$-THF, i.e., bringing said compound into a composition having a pH of 5 to 10.5, preferably 7.5 to 10.5, preferably combining said compound with a buffer, which is preferably citrate, and wherein preferably the pH is adjusted to a slightly acidic to basic pH, e.g., 5 to 10.5, preferably 7.5 to 10.5.

The stabilization of (6R)—$CH_2$-THF and of the hemisulfate salt of (6R)-5,10-$CH_2$-THF with citrate at slightly acidic to basic pH values is due to a synergistic effect of the citrate buffer solution in this pH range. Thus, even without the exclusion of atmospheric oxygen, (6R)—$CH_2$-THF solutions and solutions of hemisulfate salt of (6R)-5,10-$CH_2$-THF are stable for hours. Whereas compositions of 5,10-methylenetetrahydrofolic acid using acetate, oxalate, maleate and salts of other acids instead of citrate do not show this effect. This is also in contrast to the situation for 5-formyltetrahydrofolic acid, where an effect comparable with that of citrate can be obtained with acetate (EP 0 755 396). In 5-formyltetrahydrofolic acid solutions citrate reduces hydrolysis and oxidative cleavage of the basic skeleton and thus reduces the formation of products such as p-aminobenzoylglutamic acid and pterin- and tetrahydropterin derivatives.

In contrast to this, for (6R)—$CH_2$-THF and for the hemisulfate salt of (6R)—$CH_2$-THF in the slightly acidic to basic pH region citrate inhibits the separation of formaldehyde (hydrolysis) from the molecule. This is a difference in the behaviour of these compounds, all of which form part of the folate class of substances.

Complex formation between citrate and 5,10-methylenetetrahydrofolate on the one hand and between citrate and the counter ion (salt) of 5,10-methylenetetrahydrofolate on the other hand makes a decisive contribution to the stabilization of the methylene group by inhibiting the separation of formaldehyde (hydrolysis) from the 5,10-methylenetetrahydrofolate molecule. The formation of tetrahydrofolic acid, which is extremely sensitive to oxidation, is thereby prevented, as is the decomposition of 5,10-methylenetetrahydrofolate.

Other buffers than citrate may be for example TRIS; N-tris(hydroxymethyl) methyl-2-aminoethanesulfonic acid (TES); 3-(N-morpholino) propanesulfonic acid (MOPS); N,N-bis(2-hydroxyethyl)-2-aminoethanesulfonic acid (BES); MES; MOPSO; HEPES; phosphate; acetate; succinate; carbonate; ammonium; mono-, di- and tri-alkylammonium; mono-, di- and tri-hydroxylalkylammonium; maleate; glutamate; borate; lactate, as well as combinations of these.

In an aspect, the compositions disclosed herein, which includes the lyophilisates and well as reconstituted solutions prepared from said lyophilisates, the pH is set within the range from 5 to 10.5, preferably 7.5 to 10.5, and preferably 8.5-9.5. This is effected with the aid of aqueous sodium hydroxide and hydrochloric acid in the solution of (6R)-5,10-$CH_2$-THF and the hemisulfate salt of (6R)-5,10-$CH_2$-THF, which contain citric acid, sodium dihydrogen citrate or tri-sodium citrate dihydrate as stabilization and buffer substances. It is also possible to add reducing agents, such as L(+)-ascorbic acid or salts thereof, reduced γ-glutathione, β-mercaptoethanol, thioglycerol, N-acetyl-L-cysteine, etc. as antioxidants. In further aspects, the pH range may be broadened to include close to neutral pH values as well as slightly acidic pH values or even somewhat more basis pH values, especially in the case of the hemisulfate salt of (6R)-5,10-$CH_2$-THF, e.g., pH values of e.g., 4.0, 4.5, 5.0, 5.5, 6.0, 6.5, 6.75, 7.0, and 7.25 as well as 11 and 11.5 and ranges encompassing them, e.g., 4.0 to 11.5, and 6.5 to 10.5, more preferably 7.0 to 9.0, as well as 6.75 to 7.25.

The disclosed formulations are also particularly suitable for producing lyophilisation solutions and lyophilisates or dry powders and dry mixtures, since the stable solutions of (6R)-5,10-$CH_2$-THF and of the hemisulfate salt of (6R)-5, 10-$CH_2$-THF can be used in high concentrations for filling corresponding vessels, e.g. vials, ampoules, etc. The lyophilisates can be stored well, and are stable. They can be reconstituted without problems by the addition of water or aqueous solutions, and the final clear injection solutions such as the reconstituted solutions of lyophilisates having been prepared from the hemisulfate salt of (6R)-5,10-CH$_2$-THF again exhibits excellent stability properties.

The formulations disclosed herein are preferably used for parenteral administration. However, formulations are also produced for enteral (e.g. oral, sublingual or rectal) administration or for topical (e.g. transdermal) application.

The formulations are preferably used directly as water-based solutions or oil-based suspensions, or as lyophilisates. Preparations for parenteral application comprise sterile, aqueous and non-aqueous injection solutions and suspensions of the active compounds which preferably comprise an isotonic composition.

The formulations can also be administered with a carrier, however. Suitable carriers include organic or inorganic substances which do not react with the active ingredient, e.g. oil, benzyl alcohol, polyethylene glycol, glycerol triacetate or other fatty acid glycerides, gelatine, lecithin, cyclodextrins, carbohydrates such as lactobiose or starch, magnesium stearate, talc or cellulose. Tablets, dragees, capsules, powders, syrups, concentrates or drops are preferred for oral application, and suppositories are preferred for rectal application.

Suspensions, emulsions or implants can also be used, and patches or creams can be used for topical application.

The preparations can comprise stabilisers, additives for the controlled release of pharmaceutically active compounds, antioxidants, buffers, bacteriostatic agents and adjuvants for obtaining an isotonic solution. Aqueous and non-aqueous sterile suspensions can contain suspension additives and thickeners. The preparation can exist as a single-dose or as a multiple-dose container, e.g. as welded ampoules or vials with a stopper and a closure cap. They can be stored as a freeze-dried product and when required can be prepared for use by adding a sterile liquid, e.g. water or a physiological salt solution. Sterile powders, granules or tablets can also be used in this manner.

All preparations can additionally contain one or more separately or synergistically acting active compounds. In particular, these include fluorinated pyrimidine bases such as 5-fluorouracil (5-FU), capecitabine (Xeloda), tegafur, UFT, doxifluridine, 2,-deoxy-5-fluorouridine, various cytostatic agents such as gemcitabine (Gemzar), docetaxel (Taxotere), paclitaxel (Taxol), topotecan (Hycamtin), irinotecan (CPT-11), doxorubicin (Rubex), mitomycin (MTC), cisplatin (CDDP), cyclophosphamide (CPM), methotrexate (Amethopterin), pemetrexed (Alimta), vincristine (VCR), cytarabine (Ara-C), epirubicin (Ellence), oxaliplatin (Eloxatin), tamoxifen (Nolvadex), carboplatin (CBDCA), etoposide (Etopophos), ifosfamide (Ifex) or antioxidants such as vitamin C, vitamin E, glutathione, thioglycerol and acetylcysteine, as well as the two 5,10-MTHF dissociation products formaldehyde and tetrahydrofolic acid.

The preparation comprises between 10 mg and 3,000 mg (6R)-5,10-CH$_2$-THF daily dose.

The dosage depends on the form of therapy, on the form of application of the preparation, and on the age, weight, nutrition and condition of the patient. Treatment can commence with a smaller amount, below the optimum amount, which can be increased in order to achieve the optimum effect. The preferred dose used in therapy ranges between 10 mg and 3,000 mg per day, particularly between 100 mg and 500 mg per day. Administration can be effected either as a single dose or as a repeated dose.

The preparations can be used in all fields of application for folates.

The following examples can be carried out with a similar degree of success by replacing the generic or specifically described products and/or process conditions by those which are given in the following examples. The following specific embodiments are likewise purely exemplary and should by no means be considered as having a limiting effect on the remainder of the disclosure.

SECOND SET OF EXAMPLES

Example 2-1

A Lyophilisate Containing 5,10-Methylene-(6R,S)-Tetrahydrofolic Acid 9900 ml water were saturated with argon. 421.9 g citric acid were completely dissolved therein with stirring. 232.0 g 5,10-methylene-(6R,S)-tetrahydrofolic acid, calcium salt were added. The pH was adjusted to 8.0 with aqueous sodium hydroxide, whereupon the 5,10-methylene-(6R,S)-tetrahydrofolic acid was slowly dissolved. Thereafter, the pH was adjusted to 8.5 with aqueous sodium hydroxide. The solution was filtered under sterile conditions and was introduced at 5.0 ml per vial into 10 ml glass vials. Thereafter, the solution was frozen and freeze-dried.

Vials were obtained which contained 5,10-methylene-(6R,S)-tetrahydrofolic acid.

Example 2-2

Stabilization of 5,10-Methylene-(6R)-Tetrahydrofolic Acid (Lyophilisate)

In order to determine the long-term stabilities of (6R)-5,10-CH$_2$-THF hemisulfate salt as pharmaceutical compositions, more specifically as lyophilisates (as prepared according to e.g. Example 1-5), lyophilisates were stored in air at 25° C. and at 60% relative humidity. The content of (6R)-5,10-CH$_2$-THF hemisulfate salt remaining was measured by HPLC at periodic intervals and is given by comparison with the initial value (% rel.). The results are shown in Table 12.

TABLE 12

Long-term stability of five different production batches of (6R)-5,10-CH$_2$-THF hemisulfate salt as a lyophilisate.

| | (6R)-5,10-CH$_2$-THF hemisulfate (% rel.) | | | | | | |
| --- | --- | --- | --- | --- | --- | --- | --- |
| | 0 months | 3 months | 6 months | 9 months | 12 months | 18 months | 24 months | 36 months |
| (6R)-5,10-CH$_2$-THF hemisulfate (batch A) | 100.0 | 100.1 | 100.2 | 99.9 | 100.0 | 99.7 | 100.0 | |

TABLE 12-continued

Long-term stability of five different production batches
of (6R)-5,10-CH$_2$-THF hemisulfate salt as a lyophilisate.

| | (6R)-5,10-CH$_2$-THF hemisulfate (% rel.) | | | | | | | |
|---|---|---|---|---|---|---|---|---|
| | 0 months | 3 months | 6 months | 9 months | 12 months | 18 months | 24 months | 36 months |
| (6R)-5,10-CH$_2$-THF hemisulfate (batch B) | 100.0 | 100.1 | 99.9 | 100.0 | 99.8 | 99.7 | 100.1 | |
| (6R)-5,10-CH$_2$-THF hemisulfate (batch C) | 100.0 | 99.6 | 99.7 | 99.8 | 99.5 | 99.6 | 99.2 | 98.6 |
| (6R)-5,10-CH$_2$-THF hemisulfate (batch D) | 100.0 | 100.0 | 99.8 | 99.4 | 99.4 | 99.3 | 99.2 | 99.4[1] |
| (6R)-5,10-CH$_2$-THF hemisulfate (batch E) | 100.0 | 100.1 | | | 99.7 | | 99.4 | 98.9 |

[1] Value for 45 months

Table 12 clearly is showing that (6R)-5,10-CH$_2$-THF hemisulfate is highly stable over a long period of time even at room temperature in form of a pharmaceutical composition such as a lyophilisate.

Example 2-3

Stabilization of 5,10-Methylene-(6R,S)-Tetrahydrofolic Acid (Solutions)

Compositions prepared as in Example 2-1 exhibited the following stability values as a dilute solution in physiological common salt solution (AC0448):
Storage at +25° C. (% relative stability)
Without the exclusion of air
Duration (hours)

| 0 | 0.67 | 1.33 | 2.0 | 2.67 | 3.33 | 4.0 | 32.2 |
|---|---|---|---|---|---|---|---|
| 100.0 | 97.6 | 95.1 | 94.6 | 93.7 | 92.1 | 89.9 | 51.8 |

Compositions prepared as in Example 2-1 exhibited the following stability values as a dilute aqueous solution (AC0447):
Storage at +25° C. (% relative stability)
Without the exclusion of air
Duration (hours)

| 0 | 0.67 | 1.33 | 2.0 | 2.67 | 3.33 | 4.0 | 32.2 |
|---|---|---|---|---|---|---|---|
| 100.0 | 97.7 | 97.0 | 96.6 | 94.8 | 93.8 | 93.3 | 70.9 |

Compositions prepared as in Example 2-1 exhibited the following stability values as a concentrated aqueous solution (AC0447):
Storage at +25° C. (% relative stability)
Without the exclusion of air
Duration (hours)

| 0 | 2.0 | 4.0 | 6.0 | 12.0 | 24.0 |
|---|---|---|---|---|---|
| 100.0 | 100.2 | 99.2 | 98.1 | 95.9 | 86.2 |

As a comparison with the above, the following stability values are given in the prior art for the calcium salt of 5,10-methylene-(6R,S)-tetrahydrofolic acid in physiological common salt solution [see Chemical Stability and Human Plasma Pharmacokinetics of Reduced Folates. Odin, E. et al. Cancer Investigation 16 (7), 447-455 (1998)].
Storage at +25° C. (% relative stability)
Duration (hours)

| | 0 | 4.0 | 24.0 | 26.0 | 48.0 |
|---|---|---|---|---|---|
| With the exclusion of air | 100.0 | 58.0 | 38.0 | 18.0 | 8.0 |
| Without the exclusion of air | 100.0 | 84 | 12.0 | 8.0 | 6.0 |

Example 2-4

Tablet Containing 5,10-Methylene-(6R)-Tetrahydrofolic Acid 990 l water were saturated with argon. 42.2 kg citric acid were completely dissolved therein with stirring. 21.4 kg 5,10-methylene-(6R)-tetrahydrofolic acid were added as the free acid. The pH was adjusted to 8.0 with aqueous sodium hydroxide, whereupon the 5,10-methylene-(6R)-tetrahydrofolic acid was slowly dissolved. Thereafter, the pH was adjusted to 8.5 with aqueous sodium hydroxide. The solution was filtered under sterile conditions and lyophilised. An amount of the lyophilisate containing 1,000 g 5,10-methylene-(6R)-tetrahydrofolic acid was pressed into tablets with 4 kg lactose, 1.2 kg starch, 0.2 kg talc and 0.1 kg magnesium stearate so that each tablet contained 100 mg 5,10-methylene-(6R)-tetrahydrofolic acid. The tablet can also be coated as a film tablet.

Example 2-5

Suppositories Containing 5-Methylene-(6R,S)-Tetrahydrofolic Acid

A lyophilisate prepared as in Example 1 and containing 500 g 5,10-methylene-(6R,S)-tetrahydrofolic acid was melted with 50 g hydroxypropylcellulose and 2 kg of semisynthetic glycerides to form suppositories so that each suppository contained 500 mg 5,10-methylene-(6R,S)-tetrahydrofolic acid.

Example 2-6

A Combination Preparation Containing 5,10-Methylene-(6R,S)-Tetrahydrofolic Acid and 5-Fluorouracil, Amongst Other Ingredients A combination preparation was produced, similarly to Examples 1, 4, 5 and 7, which in addition to the usual amount of 5,10-methylene-(6R,S)-tetrahydrofolic acid for the corresponding application also contained the usual amount of 5-fluorouracil for this application.

Example 2-7

A Lyophilisate Containing 5,10-Methylene-(6R)-Tetrahydrofolic Acid 9900 ml water were saturated with argon. 316.5 g citric acid were completely dissolved therein with stirring. 212.5 g 5,10-methylene-(6R)-tetrahydrofolic acid sulfate were added. The pH was adjusted to 8.0 with aqueous sodium hydroxide, whereupon the 5,10-methylene-(6R)-tetrahydrofolic acid was slowly dissolved. Thereafter, the pH was adjusted to 8.5 with aqueous sodium hydroxide. The solution was filtered under sterile conditions and 5.0 ml per phial was introduced into 10 ml glass vials. Thereafter, the solution was frozen and freeze-dried.

Vials were obtained which contained 5,10-methylene-(6R)-tetrahydrofolic acid.

Example 2-8

Stabilization of 5,10-Methylene-(6R)-Tetrahydrofolic Acid (Solution)

Compositions prepared as in Example 2-7 exhibited the following stability values as a concentrated aqueous solution (Am 1758-2/a);
Storage at +25° C. (% relative stability)
Without the exclusion of air
Duration (hours)

| 0 | 0.67 | 1.33 | 2.67 | 4.0 | 5.33 |
|---|---|---|---|---|---|
| 100.0 | 100.2 | 99.1 | 99.2 | 98.4 | 97.7 |

As a comparison with the above, the following stability values are given in the prior art for the calcium salt of 5,10-methylene-(6R,S)-tetrahydrofolic acid in physiological common salt solution [see Chemical Stability and Human Plasma Pharmacokinetics of Reduced Folates. Odin, E. et al. Cancer Investigation 16 (7), 447-455 (1998)].
Storage at +25° C. (% relative stability)
Duration (hours)

| | 0 | 4.0 | 24.0 | 26.0 | 48.0 |
|---|---|---|---|---|---|
| With the exclusion of air | 100.0 | 58.0 | 38.0 | 18.0 | 8.0 |
| Without the exclusion of air | 100.0 | 84 | 12.0 | 8.0 | 6.0 |

In a further aspect, the hemisulfate salt of (6R)-5,10-$CH_2$-THF is disclosed in various stabilized pharmaceutical compositions, preferably in a lyophilized form as well as in a reconstituted form, preferably in a sterile form that is suitable for injection.

Another embodiment includes the products produced by the process of lyophilizing compositions, e.g., solutions, dispersions, dry preparation, etc., that contain said hemisulfate salt of (6R)-5,10-$CH_2$-THF or were produced therefrom. Likewise, another embodiment includes the products produced by the process of reconstituting said lyophilized compositions that contain said hemisulfate salt of (6R)-5,10-$CH_2$-THF.

The lyophilized and the reconstituted products may contain some amount of the hemisulfate salt of 5,10-methylene-(6R)-tetrahydrofolic acid. Said amount of the hemisulfate salt of 5,10-methylene-(6R)-tetrahydrofolic acid may or may not be in crystalline form, e.g., may be in amorphous form or dissolved. It is possible that during lyophilization and/or reconstitution the form of the hemisulfate salt of 5,10-methylene-(6R)-tetrahydrofolic acid could change, e.g., the sulfate anions may be separated from the 5,10-methylene-(6R)-tetrahydrofolic acid. However, the ratio of the 5,10-methylene-(6R)-tetrahydrofolic acid to the sulfate ion would be generally 2:1 in the lyophilisate or reconstituted form, e.g., plus-minus 20%, 10%, 5%, 2% or 1%, and ideally 2:1, i.e., 1.6 to 2.4 moles of the 5,10-methylene-(6R)-tetrahydrofolic acid to 1 mole of the sulfate in the case of 20%.

The lyophilized and the reconstituted products may further contain some amount of the sulfate salt of 5,10-methylene-(6R)-tetrahydrofolic acid. Said amount of the sulfate salt of 5,10-methylene-(6R)-tetrahydrofolic acid may or may not be in crystalline form, e.g., may be in amorphous form or dissolved. It is possible that during lyophilization and/or reconstitution the form of the sulfate salt of 5,10-methylene-(6R)-tetrahydrofolic acid could change, e.g., the sulfate anions separated from the 5,10-methylene-(6R)-tetrahydrofolic acid.

However, even in such a case where the form of the salt is not readily identifiable in a lyophilisate or reconstituted form, the products obtained by the processes disclosed herein are within the scope of the invention. Other embodiments include products that may be further modified, e.g., by the addition of further ingredients like additional anions, e.g., sulfate, or buffers, antioxidants or vitamins.

The stabilized pharmaceutical compositions contain the hemisulfate salt of (6R)-5,10-$CH_2$-THF and additionally preferably contain a buffer, which is preferably citrate. Various buffers other than citrate may be substituted or supplemented for the citrate. Such other buffers are disclosed herein already. The citrate is preferably in the form of its sodium salt form, i.e., sodium citrate. Other salts thereof are also possible. The pH of the composition is preferably basic when a higher stability is desired, e.g., as described above. However, slightly acidic, neutral or close to neutral pH values are also possible, and even desired in certain application, for example, if the stabilized pharmaceutical composition would be intended for injection. The pH may be varied independently of the addition of a buffer to the composition, but preferably the pH is adjusted to the desired pH value in combination with the use of a buffer, e.g., sodium citrate.

Lyophilized products from the stabilized pharmaceutical compositions exhibit even further stability than said stabilized pharmaceutical compositions. Said lyophilized products contain (with the possibility of additional ingredients) sulfate, the active ingredient (6R)-5,10-$CH_2$-THF, the buffering material, e.g., citrate, and any counter ion of the buffering material, e.g., sodium, in case of the use of sodium citrate. In a preferred embodiment, said lyophilized products consist only of sulfate, the active ingredient (6R)-5,10-$CH_2$-THF, the buffering material, e.g., citrate, and any counter ion of the buffering material, e.g., sodium, in case of the use of sodium citrate.

In a further embodiment, the lyophilized product is milled or ground to a homogeneous consistency, for example, to a powder. Such powder form preferably further facilitates the dissolution of the lyophilisate upon reconstitution thereof.

The lyophilized products are generally placed in unit dosages into vials that can be readily used for reconstitution of the contents thereof, e.g., in a hospital setting.

The reconstituted products from the lyophilized products from the stabilized pharmaceutical compositions exhibit even further stability, e.g., 2, 3, 4, 5, 6 or even 24 hours or even more without significant loss of active ingredient (the results varied and were better at lower temperatures as demonstrated in the examples), e.g., maintaining the amount of active ingredient at or above 90% and more preferably at or above 95% of initial amount for several hours, including most preferably about 96%, 97% or 98%. This enables the convenient administration of the previously highly unstable active ingredient (6R)-5,10-$CH_2$-THF without having to rush to avoid significant decomposition before administration. Said reconstituted products contain the same ingredients as the lyophilized products and any that were additionally added during reconstitution, e.g., sterile water or other suitable vehicles. Further additional ingredients or active agents may optionally be added at the stage of reconstitution, e.g., antioxidants, vitamins, e.g., vitamin C, or pH adjusters to achieve a desired pH suitable for administration. Suitable pH adjusters are, for example, various inorganic bases such as sodium hydroxide, sodium bicarbonate, sodium carbonate, and the like or organic bases such as sodium citrate, sodium tartrate, sodium succinate, sodium malonate, sodium gluconate and the like. When the pH would be desired to be adjusted toward a more neutral to acidic pH, various inorganic acids such as hydrochloric acid, sulfuric acid, phosphoric acid and the like or organic acids such as acetic acid, tartaric acid, lactic acid, citric acid, succinic acid, malonic acid, oxalic acid, benzoic acid, gluconic acid, fumaric acid, sorbic acid and the like may be used.

The reconstituted products ideally completely dissolve all ingredients or form a highly stable homogeneous solution. Most likely, the active ingredient (6R)-5,10-$CH_2$-THF is not present as the hemisulfate salt of said compound, but rather the active ingredient and its anions have separated in the reconstituted product solution. However, it is not impossible that some amount of the hemisulfate salt of said compound in amorphous or crystalline form is present.

In an additional embodiment, the formulations, e.g., pharmaceutical compositions, of the hemisulfate salt of (6R)-5,10-$CH_2$-THF as described herein, as well as the lyophilized and reconstituted products are administered for the treatment of various cancer therapies as described herein either as a primary therapy or an additional therapy in conjunction with other chemotherapeutic agents. One embodiment includes methods of chemotherapy with the formulations and products of the invention alone or together with additional pharmaceutically active agents suitable for chemotherapy. Likewise, another embodiment includes formulations that contain further active agents suitable for chemotherapy. Such embodiments with additional active agents may be provided in a single composition, e.g., in the lyophilized and reconstituted products or may be provided in kits together with the lyophilized and reconstituted products. The additional active agent in the kits could be administered together with the reconstituted products, e.g., by the subsequent addition thereof to the reconstituted product, or separately therefrom.

In a further aspect, the hemisulfate salt of (6R)-5,10-$CH_2$-THF may be formulated with or without any buffers, in sodium hydroxide to get the hemisulfate into solution. Such a solution may be at a pH that is from slightly acidic to neutral to slightly basic as disclosed herein.

In a further aspect, the stable pharmaceutical compositions of the present application, e.g., lyophilisates, are provided in a syringe, which may be reconstituted to form a reconstituted form of the lyophilized hemisulfate salt of (6R)-5,10-$CH_2$-THF in said syringe, from which the reconstituted solution may be readily administered to a patient. The syringe may contain additional ingredients, including further active agents, vitamins, antioxidants, etc.

Alternatively, the lyophilisates may be provided in a vial.

In a first aspect, the invention is directed to a hemisulfate salt of 5,10-methylene-(6R)-tetrahydrofolic acid. Preferably, said hemisulfate salt has a pH of between 5 and 10.5 when dissolved in water; or is anhydrous; or is in crystalline form; or is in amorphous form; or is in solution; or is in solution and has a pH of between 5 and 10.5. Preferably, a lyophilisate is made from said solution or said solution that has a pH of between 5 and 10.5 or is prepared therefrom. When in crystalline form, preferably, the hemisulfate salt has one or more X-ray pattern peak positions at an angle of diffraction 2 theta of 4.7°, 17.9°, and 23.3° expressed in 2θ±0.2° 2θ CuKα radiation, reflection; or has a FT-Raman spectrum containing one or more peaks at wavenumbers, expressed in ±2 cm-1, of 1672, 1656, 1603, 1553, 1474, 1301, 637, 624 and 363; or has a FT-Raman spectrum substantially in accordance with FIG. 1; or has an X-ray powder diffraction pattern substantially in accordance with FIG. 2(*a*); or has an X-ray powder diffraction pattern substantially in accordance with FIG. 2(*b*). Preferably, the hemisulfate salt has a chemical purity of greater than 95%; or has a chemical purity of greater than 98%; or has a chemical purity of greater than 99%; or has a chemical purity of greater than 99.5%. In a further aspect, any of the hemisulfate salts in any aspect discussed above may be in a pharmaceutical composition. Preferably, said pharmaceutical composition further contains a buffer, which preferably is capable of maintaining a pH of the dissolved composition between pH 5 and 10.5; or is capable of maintaining a pH of the dissolved composition between pH 7.5 and 10.5. In a further aspect, the buffer is citrate, phosphate, acetate, TRIS, N-tris(hydroxymethyl) methyl-2-aminoethanesulfonic acid (TES), 3-(N-morpholino) propanesulfonic acid (MOPS), N,N-bis(2-hydroxyethyl)-2-aminoethanesulfonic acid (BES), MES, MOPSO, HEPES, succinate, carbonate, ammonium, mono-, di- or tri-alkylammonium, mono-, di- or tri-hydroxylalkylammonium, maleate, glutamate, borate, lactate or combinations thereof. Optionally, the pharmaceutical composition further contains formaldehyde or at least one antioxidant or at least one radical scavenger; or at least one further chemotherapeutic agent suitable for the treatment of cancer. Preferably, any of the pharmaceutical compositions discussed herein is lyophilized or reconstituted from a lyophilized form. Any of the pharmaceutical compositions discussed herein may be in a liquid form. The pharmaceutical composition preferably is such that the molar ratio between the (6R)-5,10-$CH_2$-THF and sulfuric acid moieties is from about 1:1 to about 2:1, most preferably about 2:1. The pharmaceutical composition in one aspect is dissolved in water or a liquid pharmaceutically acceptable vehicle, and preferably is in a form suitable for administration by injection; or has a substantially neutral pH. In yet another aspect, the invention concerns a process for preparing a lyophilized product and includes the step of lyophilizing any of the pharmaceutical compositions discussed herein. Said process preferably includes the steps of dissolving the lyophilized pharmaceutical composition in water and/or a liquid pharmaceutically acceptable vehicle. In an additional aspect, the invention concerns a method for treating cancer by administering an effective amount of any of the pharmaceutical compositions discussed herein to a patient in need thereof. Said cancer is preferably breast cancer, esophageal cancer, gastric cancer, gall bladder cancer, bile duct cancer, colon cancer, rectal cancer, colorectal cancer, osteosarcoma, liver cancer, pancreatic cancer, ovarian cancer, head and neck cancer or mesotheolioma cancer.

Even more preferably, said cancer is colon cancer, stomach cancer, breast cancer, bowel cancer, gallbladder cancer, lung cancer (specifically adenocarcinoma), colorectal cancer (CRC) including metastatic CRC, head and neck cancer, liver cancer and pancreatic cancer.

Said method includes the administration of the pharmaceutical composition in conjunction with at least one further chemotherapeutic agent suitable for the treatment of cancer. In yet a further aspect, the invention concerns a stable pharmaceutical composition that contains a hemisulfate salt of 5,10-methylene-(6R)-tetrahydrofolic acid having a pH of 5 to 10.5, preferably 7.5 to 10.5; which preferably contains a hemisulfate salt of 5,10-methylene-(6R)-tetrahydrofolic acid, and a pH adjuster that is capable of bringing the composition to a pH of 5 to 10.5, preferably 7.5 to 10.5; or contains a hemisulfate salt of 5,10-methylene-(6R)-tetrahydrofolic acid and a buffer; which buffer is preferably citrate, phosphate, acetate, TRIS, N-tris(hydroxymethyl) methyl-2-aminoethanesulfonic acid (TES), 3-(N-morpholino) propanesulfonic acid (MOPS), N,N-bis(2-hydroxyethyl)-2-aminoethanesulfonic acid (BES), MES, MOPSO, HEPES, succinate, carbonate, ammonium, mono-, di- or tri-alkylammonium, mono-, di- or tri-hydroxylalkylammonium, maleate, glutamate, borate, lactate and combinations thereof; or wherein at least some of the hemisulfate salt is in anhydrous form; or wherein at least some of the hemisulfate salt is in crystalline form; or wherein the hemisulfate salt has one or more X-ray pattern peak positions at an angle of diffraction 2 theta of 4.7°, 17.9°, and 23.3° expressed in 2θ±0.2° 2θ CuKα radiation, reflection; or wherein the hemisulfate salt has a FT-Raman spectrum containing one or more peaks at wavenumbers, expressed in ±2 cm-1, of 1672, 1656, 1603, 1553, 1474, 1301, 637, 624 and 363; or wherein the hemisulfate salt has a FT-Raman spectrum substantially in accordance with FIG. 1 and/or an X-ray powder diffraction pattern substantially in accordance with FIG. 2(a) or 2(b); or which further contains formaldehyde or at least one antioxidant or a radical scavenger; or additionally contains at least one further chemotherapeutic agent suitable for the treatment of cancer or is together in a kit with said at least one further chemotherapeutic agent. In further aspects, the invention concerns a lyophilized product that has been prepared from the stable pharmaceutical compositions discussed above, which composition has been lyophilized; wherein preferably the molar ratio between the (6R)-5,10-CH$_2$-THF and H$_2$SO$_4$ moieties is about 2:1. In a further aspect, the invention concerns a lyophilized product wherein preferably the molar ratio between the (6R)-5,10-CH$_2$-THF and H$_2$SO$_4$ moieties is about 1:1.

In an additional aspect, the invention concerns a reconstituted solution from the lyophilized product discussed above, which product has been reconstituted by water or a liquid pharmaceutically acceptable vehicle; in which reconstituted solution from the lyophilized product, preferably the molar ratio between the (6R)-5,10-CH$_2$-THF and H$_2$SO$_4$ moieties is from about 1:1 to about 2:1, most preferably about 2:1. Said reconstituted solution is preferably in a form suitable for administration by injection, and whose pH has been optionally adjusted to substantially neutral. In further aspects, the invention includes a process for preparing the lyophilized products mentioned above, which includes lyophilizing a composition that contains a hemisulfate salt of 5,10-methylene-(6R)-tetrahydrofolic acid, and a buffer, and/or a pH adjuster that is capable of bringing the composition to a pH of 5 to 10.5, preferably 7.5 to 10.5; which process optionally includes bringing a lyophilized product that has been prepared from a composition that contains a hemisulfate salt of 5,10-methylene-(6R)-tetrahydrofolic acid, and a buffer, and/or a pH adjuster that is capable of bringing the composition to a pH of 5 to 10.5, preferably 7.5 to 10.5 into a solution with water and/or a liquid pharmaceutically acceptable vehicle, such as propylene glycol, a polyethylene glycol, ethanol, dimethyl sulfoxide (DMSO), N-methylpyrrolidinone (NMP), glycofurol, isopropylidene glycerol (Solketal), glycerol formal, acetone, tetrahydrofurfuryl alcohol, monoglyme, diglyme, dimethyl isosorbide and ethyl lactate, and mixtures thereof, and aqueous mixtures thereof.

In yet a further aspect, included in the invention is a method for treating cancer by administering an effective amount of the pharmaceutical composition discussed above to a patient in need thereof; which method preferably includes administering an effective amount of said reconstituted solution to a patient in need thereof; or which method preferably concerns the treatment of breast cancer, esophageal cancer, gastric cancer, gall bladder cancer, bile duct cancer, colon cancer, rectal cancer, colorectal cancer, osteosarcoma, liver cancer, pancreatic cancer, ovarian cancer, head and neck cancer or mesotheolioma cancer; and in particular the treatment of colon cancer, stomach cancer, breast cancer, bowel cancer, gallbladder cancer, lung cancer (specifically adenocarcinoma), colorectal cancer (CRC) including metastatic CRC, head and neck cancer, liver cancer and pancreatic cancer, or preferably wherein the reconstituted solution is administered in conjunction with at least one further chemotherapeutic agent suitable for the treatment of cancer.

In an additional aspect, the invention includes a lyophilized formulation A, B, C, D or E, which A) is prepared from a hemisulfate salt of 5,10-methylene-(6R)-tetrahydrofolic acid, B) contains 5,10-methylene-(6R)-tetrahydrofolic acid and/or 5,10-methylene-(6R)-tetrahydrofolate resulting from a hemisulfate salt of 5,10-methylene-(6R)-tetrahydrofolic acid, C) contains about two moles of 5,10-methylene(6R)-tetrahydrofolic acid and/or 5,10-methylene-(6R)-tetrahydrofolate to one mole of sulfate ions, D) contains about 1 mole of 5,10-methylene-(6R)-tetrahydrofolic acid and/or 5,10-methylene-(6R)-tetrahydrofolate to one mole of sulfate ions, or E) contains 5,10-methylene-(6R)-tetrahydrofolic acid and/or 5,10-methylene-(6R)-tetrahydrofolate having a chemical purity of greater than 95%, preferably 98% and more preferably 99%, and even more preferably 99.5%, or even higher, e.g., 99.6, 99.7, 99.8 or 99.9% or above, e.g., 100, and sulfate. Preferably, the lyophilized formulation A, B, C, D or E, are used to prepare a reconstituted solution therefrom. In one aspect, the invention concerns a process for preparing said lyophilized formulation A, B, C, D or E, by lyophilizing a composition that contains a hemisulfate salt of 5,10-methylene-(6R)-tetrahydrofolic acid.

In a final aspect, the invention includes a stable pharmaceutical composition X or Y that contains 5,10-methylene-(6R)-tetrahydrofolic acid, more precisely contains X) a lyophilised hemisulfate salt of 5,10-methylene-(6R)-tetrahydrofolic acid, which has such stability that the composition maintains greater than or equal to 95%, preferably between 97-98%, and more preferably at about 99%, of purity of the 5,10-methylene-(6R)-tetrahydrofolic acid for at least 24 months, preferably for at least 36 months, and more preferably for at least 48 months at +25° C./60% relative humidity; or for at least 12 months at +40° C./75% relative humidity, or for at least 24 months, preferably at least 36 months, and more preferably for at least 48 months at +5° C., or for at least 24 months, preferably at least 36 months at −20° C.; or Y) a reconstituted lyophilised hemisulfate salt of 5,10-methylene-(6R)-tetrahydrofolic acid, which has such stability that the composition maintains greater than or equal to 95%, preferably between 95-96%, and more preferably at about 97%, of purity of the 5,10-methylene-(6R)-tetrahydrofolic acid for at least 200 minutes, preferably 6 hours, and more preferably 11 or 12 hours at 2-8° C., or for at least 2 hours, and more preferably for at least 200 minutes at room temperature.

THIRD SET OF EXAMPLES

The following abbreviations were used in the third set of examples:
ABGA 4-Aminobenzoylglutamic acid
FTHFA (6R)-10-Formyltetrahydrofolic acid
FDHFA 10-Formyldihydrofolic acid
FA Folic acid
THFA Tetrahydrofolic acid
DHFA 7,8-Dihydrofolic acid
CH2THPA 5,10-Methylenetetrahydropteric acid
rRt0.93 specified unidentified related compound at rRt 0.93
CH2THFA 5,10-Methylenetetrahydrofolic acid
rRt1.18 specified unidentified compound at rRt 1.18
rRt1.24 specified unidentified pound at rRt 1.24
5-MeTHFA 5-Methyltetrahydrofolic acid
BigUK Biggest unknown related compound
SumTot Sum total of all related compounds Example 3-1

Stability of the Lyophilised Hemisulfate Salt of 5,10-Methylene-(6R)-Tetrahydrofolic Acid The following extract of stability data concerns the stability of the lyophilised hemisulfate salt of 5,10-methylene-(6R)-tetrahydrofolic acid.

The stability study is performed according to the ICH guideline Q1A.

| | | HPLC: | | | | |
|---|---|---|---|---|---|---|
| | | Purity | | Related compounds: | | |
| | Assay | Peak + | L-10- | unknown | | sum |
| Period (months) | free acid (mg/vial) | Ramp (% area) | FTHFA (% w/w) | single (% w/w) | sum (% w/w) | total (% w/w) |
| +25° C./60% relative humidity | | | | | | |
| 0 | 101.7 | 97.75 | 0.05 | 0.09 | 0.34 | 0.70 |
| 3 | 101.6 | 97.88 | 0.05 | 0.06 | 0.31 | 0.66 |
| 6 | 101.5 | 97.92 | 0.05 | 0.05 | 0.30 | 0.65 |
| 9 | 99.3 | 97.70 | 0.05 | 0.08 | 0.34 | 0.70 |
| 12 | 102.4 | 97.71 | 0.05 | 0.06 | 0.33 | 0.71 |
| 18 | 100.1 | 97.42 | 0.05 | 0.14 | 0.37 | 0.79 |
| 24 | 101.8 | 97.71 | 0.06 | 0.05 | 0.29 | 0.73 |
| 24 | 99.8 | 96.92 | 0.06 | 0.05 | 0.42 | 0.95 |
| 36 | 100.5 | 97.63 | 0.06 | 0.06 | 0.36 | 0.73 |
| 48 | 100.9 | 97.90 | 0.06 | 0.06 | 0.30 | 0.67 |
| +40° C./75% relative humidity | | | | | | |
| 0 | 101.7 | 97.75 | 0.05 | 0.09 | 0.34 | 0.70 |
| 3 | 101.6 | 97.71 | 0.06 | 0.07 | 0.32 | 0.72 |
| 6 | 101.6 | 97.82 | 0.06 | 0.05 | 0.31 | 0.68 |
| 9 | 99.0 | 97.61 | 0.06 | 0.08 | 0.35 | 0.72 |
| 12 | 102.4 | 97.69 | 0.06 | 0.06 | 0.33 | 0.72 |
| +5° C. | | | | | | |
| 0 | 101.7 | 97.75 | 0.05 | 0.09 | 0.34 | 0.70 |
| 3 | 101.6 | 97.84 | 0.05 | 0.07 | 0.31 | 0.67 |
| 6 | 101.8 | 97.94 | 0.05 | 0.05 | 0.30 | 0.64 |
| 9 | 99.7 | 97.77 | 0.05 | 0.07 | 0.33 | 0.68 |
| 12 | 102.4 | 97.77 | 0.05 | 0.06 | 0.32 | 0.70 |
| 18 | 100.6 | 97.56 | 0.04 | 0.14 | 0.35 | 0.75 |
| 24 | 101.8 | 97.7 | 0.05 | 0.06 | 0.33 | 0.73 |
| 24 | 99.9 | 97.09 | 0.05 | 0.05 | 0.39 | 0.88 |
| 36 | 100.7 | 97.7 | 0.05 | 0.05 | 0.36 | 0.71 |
| 48 | 101.6 | 98.00 | 0.05 | 0.05 | 0.26 | 0.62 |
| −20° C. | | | | | | |
| 0 | 101.7 | 97.75 | 0.05 | 0.09 | 0.34 | 0.70 |
| 3 | 101.1 | 97.84 | 0.04 | 0.06 | 0.32 | 0.66 |
| 6 | 101.0 | 97.91 | 0.04 | 0.06 | 0.32 | 0.64 |
| 9 | 99.8 | 97.67 | 0.05 | 0.08 | 0.35 | 0.71 |
| 12 | 102.7 | 97.81 | 0.04 | 0.06 | 0.32 | 0.69 |
| 18 | 100.6 | 97.74 | 0.05 | 0.09 | 0.28 | 0.70 |
| 24 | 101.8 | 97.73 | 0.04 | 0.07 | 0.33 | 0.70 |
| 24 | 100.1 | 97.02 | 0.05 | 0.05 | 0.40 | 0.92 |
| 36 | 100.0 | 97.77 | 0.05 | 0.05 | 0.34 | 0.68 |

The HPLC purity results clearly demonstrate the exceptionally good stability of the lyophilised hemisulfate salt of 5,10-methylene-(6R)-tetrahydrofolic acid up to 24 months of testing at various tested conditions.

Example 3-2

Stability of the Reconstituted Lyophilised Hemisulfate Salt of 5,10-Methylene-(6R)-Tetrahydrofolic Acid from Vials The following stability data concerns the stability of the reconstituted lyophilised hemisulfate salt of 5,10-methylene-(6R)-tetrahydrofolic acid from vials.

The test concern reconstituted lyophilised hemisulfate salt of 5,10-methylene-(6R)-tetrahydrofolic acid powder for solution for injection 100 mg in order to determine whether sufficient stability is present after reconstitution for a sufficient time for use.

Two vials were used for each storage condition.
The following tests are performed on the reconstituted vials:
Appearance of solution (Visual)
Colour of solution (UV, 420 nm, 4 cm)
Assay/Purity and related compounds (HPLC)
Test conditions and frequencies were as follows:
Room temperature: Initial (0 h), 1 h, 2 h, 3 h, 4 h, 5 h, 6 h, and 24 h
2° C.–8° C.: Initial (0 h), 6 h, and 24 h Results for related compounds and UV absorption are rounded to two decimals. Purity and Assay are rounded to zero decimals in accordance with the corresponding specifications.

In all vials the cake rapidly dissolved after addition of water. No precipitation was observed during the study.

| Room temperature; Summary of plotted HPLC results | | | |
|---|---|---|---|
| Parameter | Trend description of plot | Comment on plot | Spec. [%] |
| ABGA | linear increase | within specification up to approx. 10.5 hrs | ≤0.8% w/w |
| FTHFA | initial decrease, then slow increase | no significant change relative to specification | ≤1.0% w/w |
| FDHFA | fast initial increase, slows after 6 hrs | no significant change relative to specification | ≤0.8% w/w |
| FA | stable within first 6 hrs, then increasing | no significant change relative to specification | ≤0.8% w/w |
| THFA | initial increase, then slow decrease | no significant change relative to specification | ≤0.8% w/w |
| DHFA | fast initial increase, slows after 6 hrs | within specification up to 6 hrs | ≤0.8% w/w |
| CH2THPA | small decrease (stable) | no significant change relative to specification | ≤1.0% w/w |
| rRt0.93 | small decrease (stable) | no significant change relative to specification | ≤0.10% w/w |
| Purity | linear decrease | within specification up to 2 hrs | ≥95% area |
| Assay | linear decrease | within specification up to approx. 10.5 hrs | 90-110 mg/Vial |
| rRt1.18 | overall small increase | no significant change relative to specification | ≤0.10% w/w |
| rRt1.24 | linear increase | within specification up to 4 hrs | ≤0.10% w/w |
| 5-MeTHFA | small changes (stable) | no significant change relative to specification | ≤0.5% w/w |
| BigUK | first slow, then faster increase, | within specification up to 5 hrs | ≤0.10% w/w |
| SumTot | linear increase | within specification up to approx. 7.5 hrs | ≤3.0% w/w |

Stability at Room Temperature

Both vials show a very similar stability behaviour. The reconstituted solution is constantly clear (no precipitation) and the colour changes from yellowish to a dark neon-yellow over the investigated time period. This result is confirmed by an increase of UV absorption at 420 nm. The tabulated results show, that after reconstitution all of the related compounds remain within release specification for 4 hours. Assay and "Sum of all related compounds" are within specification up to 6 hours and the Purity up to 2 hours.

Based on the slope of a regression equation the Purity decreased at a rate of 0.86% per hour.

| 2° C. to 8° C.; Summary of plotted HPLC results | | | |
|---|---|---|---|
| Parameter | Trend description of plot | Comment on plot | Spec. [%] |
| ABGA | small increase (stable) | no significant change relative to specification | ≤0.8% w/w |
| FTHFA | small decrease (stable) | no significant change relative to specification | ≤1.0% w/w |
| FDHFA | small increase (stable) | no significant change relative to specification | ≤0.8% w/w |
| FA | small increase (stable) | no significant change relative to specification | ≤0.8% w/w |
| THFA | small variations (stable) | no significant change relative to specification | ≤0.8% w/w |
| DHFA | linear increase | no significant change relative to specification | ≤0.8% w/w |
| CH2THPA | small decrease | no significant change relative to specification | ≤1.0% w/w |
| rRt0.93 | small variations (stable) | no significant change relative to specification | ≤0.10% w/w |
| Purity | linear decrease | within specification up to approx. 12 hrs | ≥95% area |
| Assay | linear decrease | no significant change relative to specification | 90-110 mg/Vial |
| rRt1.18 | overall small increase | remains within specification | ≤0.10% w/w |
| rRt1.24 | linear increase | no significant change relative to specification | ≤0.10% w/w |
| 5-MeTHFA | small decrease | no significant change relative to specification | ≤0.5% w/w |
| BigUK | small increase | no significant change relative to specification | ≤0.10% w/w |
| SumTot | linear increase | no significant change relative to specification | ≤3.0% w/w |

Stability at 2° C. to 8° C.

Again both vials show a very similar stability behaviour. The reconstituted solution is constantly clear and the colour changes from yellowish to a dark neon-yellow over the investigated time period. This result is confirmed by an increase of UV absorption at 420 nm. The tabulated results show, that after reconstitution Assay, all individual related compounds, as well as "Sum of all related compounds" remain within release specification for 24 hours. The Purity is within the acceptance limit up to 6 hours.

Based on the slope of a regression equation the Purity decreased at a rate of 0.12% per hour. Thus the degradation rate at 2-8° C. is 7 times slower than the rate at room temperature.

When applying the drug product release specification, the main determining stability parameter is the Purity. Based on the applied test interval in-use stability of 2 hours at room temperature and 6 hours at 2-8° C. is validated.

However, the rate of degradation can be described by linear regression with a regression coefficient of >0.99. Extrapolation of the data based on the regression formula gives further information on the decrease of the Purity. The formulae are as follows:

Purity [area %]=96.4−0.8556×Time [h]  At room temperature:

Purity [area %]=95.9−0.1218×Time [h]  At 2° C. to 8° C.:

Application gives the following calculated results:

Example 3-3

Stability of Reconstituted Lyophilised Hemisulfate Salt of 5,10-Methylene-(6R)-Tetrahydrofolic Acid Powder for Solution for Injection 100 mg in Plastic Syringes The following tests concern the stability of reconstituted lyophilised hemisulfate salt of 5,10-methylene-(6R)-tetrahydrofolic acid powder for solution for injection 100 mg in plastic syringes in order to determine an in-use shelf-life of the drug product after reconstitution and transfer to the syringe. The syringes containing the reconstituted drug product have been stored at two different storage conditions, room temperature and 2° C. to 8° C.

Two vials were used for each storage condition.

Plastic syringes (10 mL, BD Plastipak with Luer-Lok™ tip) were supplied by Sykehusapotheket Oslo.

Assay/Purity and related compounds (HPLC) were determined on the reconstituted solution taken from the syringes. At each time-point 1 mL of drug product solution (according to graduation scale on the syringe) was taken from the syringe and diluted 50-fold in two steps for the HPLC measurements.

Test conditions and frequencies were as follows:
Room temperature [15-25° C.]: Initial (0 min), 50 min, 100 min, 150 min, and 200 min
Refrigerated [2° C.–8° C.]: Initial (0 min), 50 min, 100 min, 150 min, and 200 min

| Purity results calculated from regression equations | | | | | | | | | | | | | | | | | | | | | | | |
|---|---|---|---|---|---|---|---|---|---|---|---|---|---|---|---|---|---|---|---|---|---|---|---|
| | Time [h] | | | | | | | | | | | | | | | | | | | | | | |
| | 0 | 0.5 | 1 | 1.5 | 2 | 2.5 | 3 | 3.5 | 4 | 4.5 | 5 | 5.5 | 6 | 6.5 | 7 | 7.5 | 8 | 8.5 | 9 | 9.5 | 10 | 10.5 | 11 |
| RT, Purity [% area] | 96 | 96 | 96 | 95 | 95 | 94 | 94 | 93 | 93 | 93 | 92 | 92 | 91 | 91 | 90 | 90 | 90 | 89 | 89 | 88 | 88 | 87 | 87 |
| 2-8° C., Purity [% area] | 96 | 96 | 96 | 96 | 96 | 96 | 96 | 95 | 95 | 95 | 95 | 95 | 95 | 95 | 95 | 95 | 95 | 95 | 95 | 95 | 95 | 95 | 95 |

The regression data above show that, based on the Purity specification, the reconstituted drug product is stable up to 11 hrs at 2-8° C. The 2 hour stability at room temperature is confirmed. At 2-8° C. the Purity remains at 96% and above up to 3 hours. In addition, the Purity is stable up to 2 hours at room temperature with an initial value of 96%. Thus, based on this data a combination of storage conditions, e.g. 3 hours at 2-8° C. plus 2 hours at room temperature, would be justified.

Based on the present stability investigation the following conclusions regarding the stability of reconstituted drug product vials are justified:

2 hour stability at room temperature 6 hour stability at 2-8° C. (11 hours based on linear regression)

Regression data indicates that a combined storage condition of 3 hours at 2-8° C. plus 2 hours at room temperature is justified.

Longer stability times could be achieved if a lower Purity specification would be acceptable for the in-use stability.

Results for related compounds are rounded to two decimals. Purity and Assay are rounded to zero decimals in accordance with the corresponding specifications for the lyophilised hemisulfate salt of 5,10-methylene-(6R)-tetrahydrofolic acid drug product.

Test results are compared to the product release specifications of the lyophilised hemisulfate salt of 5,10-methylene-(6R)-tetrahydrofolic acid powder for solution for injection 100 mg where applicable.

At each temperature condition both syringes show a similar stability behavior. However, Purity and Assay (mg/Vial) show some variation which is most likely due to imprecision introduced by using the syringe graduation for measurement of the 1 mL portion at the individual time-points. The study design included 2 syringes at each storage condition to calculate the mean value for the stability evaluation. The stability evaluation is based on the mean values.

In all vials the cake rapidly (<1 min) dissolved after addition of water. No precipitation was observed in the syringes during the study.

| Room temperature; Summarized trend descriptions ||||
| --- | --- | --- | --- |
| Parameter | Trend description | Comment | Specification |
| ABGA | fast initial increase, slows after 50 min | no significant change relative to specification | ≤0.8% w/w |
| FTHFA | stable | no significant change at all | ≤1.0% w/w |
| FDHFA | stable | no significant change at all | ≤0.8% w/w |
| FA | not detected (stable) | no change at all | ≤0.8% w/w |
| THFA | fast initial increase, slows after 50 min | no significant change relative to specification | ≤0.8% w/w |
| DHFA | fast initial increase, slows after 50 min | no significant change relative to specification | ≤0.8% w/w |
| CH2THPA | stable | no significant change at all | ≤1.0% w/w |
| rRt0.93 | stable | no significant change relative to specification | ≤0.10% w/w |
| Purity | fast initial decrease, then stable | within specification up to 200 min | ≥95% area |
| Assay* | varies up and down | within specification up 200 min | 90-110 mg/Vial |
| rRt1.18 | stable | no significant change at all | ≤0.10% w/w |
| rRt1.24 | linear increase | no significant change relative to specification | ≤0.10% w/w |
| 5-MeTHFA | no clear trend | no significant change relative to specification | ≤0.5% w/w |
| BigUK | slow increase, | no significant change relative to specification | ≤0.10% w/w |
| SumTot | fast initial increase, slows after 50 min | no significant change relative to specification | ≤3.0% w/w |

*Assay (mg/vial) strongly depends on the accuracy of the pipetting and dilution steps. Due to using the syringe graduation for measurement of the 1 mL portion at the individual time-points the parameter strongly varies and is not suitable for the evaluation of sample stability.

Stability at Room Temperature

The tabulated mean results show, that at room temperature all mean values were within specification over the investigated time period of 200 min (3 hours and 20 minutes). The Purity decreases markedly in the first 50 min and then reaches an almost stable plateau at 100 min. All values are within the limit for 200 min. The slope of the regression line (for the plateau) indicates a slower decrease than in the vial. Interestingly the slope is exactly the same, as at 2-8° C., once the plateau is reached (−0.0009% Purity/min).

Generally, these results are comparable with the stability data for the in-use vial stability of the drug product.

| 2° C. to 8° C.; Summarized trend descriptions ||||
| --- | --- | --- | --- |
| Parameter | Trend description | Comment | Specification |
| ABGA | fast initial increase, slows after 50 min | no significant change relative to specification | ≤0.8% w/w |
| FTHFA | stable | no significant change at all | ≤1.0% w/w |
| FDHFA | stable | no significant change at all | ≤0.8% w/w |
| FA | not detected (stable) | no change at all | ≤0.8% w/w |
| THFA | Slow decrease | no significant change relative to specification | ≤0.8% w/w |
| DHFA | fast initial increase, slows after 50 min | no significant change relative to specification | ≤0.8% w/w |
| CH2THPA | stable | no significant change at all | ≤1.0% w/w |
| rRt0.93 | stable | no significant change relative to specification | ≤0.10% w/w |
| Purity | decrease after 50 in, then stable | within specification up to 200 min | ≥95% area |
| Assay* | varies up and down | All values except 100 min within specification* | 90-110 mg/Vial |
| rRt1.18 | stable | no significant change at all | ≤0.10% w/w |
| rRt1.24 | linear increase | no significant change relative to specification | ≤0.10% w/w |
| 5-MeTHFA | no clear trend | no significant change relative to specification | ≤0.5% w/w |
| BigUK | slow increase, | no significant change relative to specification | ≤0.10% w/w |
| SumTot | fast initial increase, slows after 50 min | no significant change relative to specification | ≤3.0% w/w |

*Assay (mg/vial) strongly depends on the accuracy of the pipetting and dilution steps. Due to using the syringe graduation for measurement of the 1 mL portion at the individual time-points the parameter strongly varies and is not suitable for the evaluation of sample stability.

Stability at 2° C. to 8° C.

The tabulated mean results show, that at refrigerated temperature all parameters, except Assay at 100 min, were within specification over the investigated time period of 200 min. At 100 min a mean Assay value of 87 mg/vial was found. However, mean values before and after 100 min are within specification. Therefore, it can be strongly assumed that the 100 min result is not representative for the real loss of concentration. Assay (mg/vial) strongly depends on the accuracy of the pipetting and dilution steps. Because the syringe graduation was used for measurement of the 1 mL portion at the individual time-points the Assay varies markedly and is not suitable for the evaluation of sample stability. Consequently, the focus was placed on the Purity.

Data shows that the Purity decreases in the first 100 min and then remains almost constant until 200 min (3 hours and 20 minutes). Extrapolation of the last 3 data points (when the stability plateau is reached) indicates that the stability up to 360 min is equal to the "in-use vial stability" of the drug product (6 hours at 2-8° C.). The slope of the regression line decreases with −0.0009% Purity/min, which is equal to the decrease at room temperature.

When applying the drug product release specification, the main determining stability parameter is the Purity.

Real time data show, both at 2-8° C. and 15-25° C., a stability plateau at 100 min. At both conditions the real time Purity data is within specification up to 200 min.

Moreover, the extrapolation results for the Purity show that based on the equality of the slopes at both temperature conditions it can be deducted that the reconstituted drug product stored in a syringe at 2-8° C. for 200 min could subsequently be placed at room temperature without a marked impact on the degradation rate. The slope of the degradation can be expected to remain at −0.0009%/min.

Consequently, a combined syringe storage time of 3 hours (180 min) at 2-8° C. and then additional 3 hours (180 min) at 15-25° C. seems viable based on the extrapolated Purity data. Alternatively, a storage time of 6 hours at 2-8° C. would also be justified by the extrapolated data.

Example 3-4

Stability of Lyophilised Hemisulfate Salt of 5,10-Methylene-(6R)-Tetrahydrofolic Acid at High Concentration, 75 mg/ml, in a pH Adjusted Formulation Buffer The present report investigates the stability of lyophilised hemisulfate salt of 5,10-methylene-(6R)-tetrahydrofolic acid drug substance at high concentration, 75 mg/ml, in a pH adjusted formulation buffer. The buffer composition used is essentially the same as for the lyophilised hemisulfate salt of 5,10-methylene-(6R)-tetrahydrofolic acid drug product except that additional sodium hydroxide was added for pH adjustment. The goal of this report is to investigate the stability of a lyophilised hemisulfate salt of 5,10-methylene-(6R)-tetrahydrofolic acid drug substance solution at 75 mg/ml and to provide information for a preparation and handling description of the formulation for toxicology studies. The buffered lyophilised hemisulfate salt of 5,10-methylene-(6R)-tetrahydrofolic acid solutions were stored at two different storage conditions, room temperature and 2° C. to 8° C. (refrigerator).

For each storage condition one sample solution was prepared.

Storage conditions and frequencies were as follows:

Room temperature [15-25° C.]: Initial (0), 50, 100, 150, 200, 250, 350, and 1440 min Refrigerated [2° C.–8° C.]: Initial (0), 50, 100, 150, 200, 250, 350, and 1440 min The formulation buffer was prepared as follows:

4.61 g Trisodium Citrate Dihydrate 7.26 g 2M Sodium hydroxide 89.88 g milli-Q water Mix well and measure pH after complete dissolution to approximate pH 13.0

The lyophilised hemisulfate salt of 5,10-methylene-(6R)-tetrahydrofolic acid drug substance solution (sample solution) was prepared as follows:

Determine tare weight of empty flask.

Target value is to reach a total added weight of 50 g including lyophilised hemisulfate salt of 5,10-methylene-(6R)-tetrahydrofolic acid drug substance and added solutions.

Add 3500 mg lyophilised hemisulfate salt of 5,10-methylene-(6R)-tetrahydrofolic acid drug substance Add about 30 g formulation buffer and mix well, a turbid solution is obtained, pH approximately 4.5

Adjust pH to approximately 9.3 with sodium hydroxide solution ≥32% (Sigma Aldrich #30531)

This gives a clear solution.

Add formulation buffer to total weight of about 50 g, the pH increases to approximately 10.5

Adjust pH to 9.8 with 0.1 M hydrochloric acid solution

Determine final weight and density of final sample solution.

(at 5° C.: weight 50.02 g, density 1.0680 g/mL; at 20° C.: weight 50.1 g, density 1.06540 g/mL)

Final concentration of drug substance calculates to 75 mg/mL.

Time from start of dissolution to final pH adjustment: approximately 10-20 min The sample solution for the investigation at 2° C.-8° C. was prepared at room temperature to avoid temperature dependent differences in solubility time. After preparation this solution was immediately placed in a refrigerator.

For HPLC measurement of lyophilised hemisulfate salt of 5,10-methylene-(6R)-tetrahydrofolic acid Purity, Assay free acid and related compounds (HPLC) a 2 mL sample was taken at each time-point from the test solution and diluted in two steps to a final concentration of approximately 0.24 mg/mL.

An acceptable limit of "purity ≥95%" was applied as stability criterion.

Generally, it can be concluded that the sample solution stability is better at 2-8° C. than at 20-25° C. After dissolution of the lyophilised hemisulfate salt of 5,10-methylene-(6R)-tetrahydrofolic acid drug substance the solutions were clear and had a light yellowish color. No precipitation was observed in the solution during the investigation either stored in the refrigerator or at RT.

| \multicolumn{3}{l}{Room temperature; Summarized trend descriptions} |
| --- | --- | --- |
| Analytical Parameter | Trend description | Limit* |
| Purity | Almost constant decrease. Within specification up to 200 min. | ≥95% area* |
| CH2THFA free acid | Initially slow decrease until 350 min, then unexpected increase at 24 hours. | n/a |
| ABGA** | Slow initial increase until 350 min, then slope increases (approx. 8-fold in 24 hours). | ≤0.8% w/w |
| FTHFA** | Slow decrease (approximately by a factor of 0.25 in 24 hours). | ≤1.0% w/w |
| FDHFA** | Almost constant increase (approximately 5-fold in 24 hours). | ≤0.8% w/w |
| FA** | Not detected (stable) | ≤0.8% w/w |
| THFA** | Small initial increase than constant decrease (approx. by a factor of 0.5 in 24 hours). | ≤0.8% w/w |
| DHFA | Fast initial then constant increase (approximately 15-fold in 24 hours). | ≤0.8% w/w |
| CH2THPA** | No marked change (stable). | ≤1.0% w/w |
| rRt0.93** | No marked change (stable). | ≤0.5% w/w |
| rRt1.18** | Initially stable until 350 min, then small increase (approx. 1.5-fold in 24 hours). | ≤0.5% w/w |
| rRt1.24 | Initially slow increase until 350 min, then slope increases (approx. 6-fold in 24 hours). | ≤0.5% w/w |
| 5-MeTHFA** | Initially stable until 350 min, then small increase (approx. 1.5-fold in 24 hours). | ≤0.5% w/w |
| BigUK | Initially slow increase until 350 min, then slope increases (approx. 5-fold in 24 hours). | ≤0.5% w/w |
| SumTot | Almost constant increase (approximately 4-fold in 24 hours). | ≤3.0% w/w |

*according to predetermined specification
**remains within specification

Stability at Room Temperature

During the investigation the color of solution darkened continuously. After 24 hours the solution stored at room temperature had changed from light yellowish to orange. No protection from light was used.

The Purity constantly decreases during storage at room temperature. Up to 200 minutes (3.3 hours) the Purity remains within the defined limit of "not less than 95% Area". The lyophilised hemisulfate salt of 5,10-methylene-(6R)-tetrahydrofolic acid Assay free acid initially shows a slow decrease until 350 min (5.8 hours).

unexpected, rapid initial decrease is most likely not related to the degradation of the drug substance.

The goal of this study was to investigate the stability of high concentration lyophilised hemisulfate salt of 5,10-methylene-(6R)-tetrahydrofolic acid solution (75 mg/ml) to be used in toxicology studies. Some of the related compounds did increase during the storage. The stability evaluation is based on Purity (not less than 95%). The main focus of the discussion is therefore focused on this parameter.

The lyophilised hemisulfate salt of 5,10-methylene-(6R)-tetrahydrofolic acid free acid content showed an unexpected

| \multicolumn{3}{l}{2° C. to 8° C.; Summarized trend descriptions} |
| --- | --- | --- |
| Analytical Parameter | Trend description | Limit* |
| Purity | Slow but constant decrease. Within specification up to 24 hours. | ≥95% area* |
| CH2THFA free acid | Initially rapid decrease until 50 min (approx. 10%), then almost constant. | n/a |
| ABGA** | Slow & minor increase over 24 hours. | ≤0.8% w/w |
| FTHFA** | Slow & minor decrease over 24 hours. | ≤1.0% w/w |
| FDHFA** | Almost constant increase (approximately 2-fold in 24 hours). | ≤0.8% w/w |
| FA** | Not detected (stable) | ≤0.8% w/w |
| THFA** | Almost constant decrease (approx. by a factor of 0.5 in 24 hours). | ≤0.8% w/w |
| DHFA | Almost constant increase (approximately 3-fold in 24 hours). | ≤0.8% w/w |
| CH2THPA** | No marked change (stable). | ≤1.0% w/w |
| rRt0.93** | No marked change (stable). | ≤0.5% w/w |
| rRt1.18** | Minor variations (stable) | ≤0.5% w/w |
| rRt1.24** | Slow & minor decrease over 24 hours. | ≤0.5% w/w |
| 5-MeTHFA** | Minor variations (stable) | ≤0.5% w/w |
| BigUK** | Minor variations (stable) | ≤0.5% w/w |
| SumTot | Slow but constant increase (approximately 1.5-fold in 24 hours). | ≤3.0% w/w |

*according to predetermined specification
**remains within specification

Stability at 2° C. to 8° C.

During the investigation the color of solution darkened continuously. After 24 hours the solution stored under refrigeration had changed from light yellowish to an intense yellow. The Purity decreases slowly but constantly during storage 2-8° C. However, up to 24 hours the Purity remains within the defined acceptance limit of "not less than 95% Area". After a high initial result, the lyophilised hemisulfate salt of 5,10-methylene-(6R)-tetrahydrofolic acid free acid drops to about 10% w/w after 50 min and then remains almost constant over the 24 hours investigation period. The behavior during the stability investigation. The sample solution stored at room temperature showed a marked increase of content about 10% w/w at the 24 hour time-point, and for the sample solution stored at 2-8° C. there was a higher content value for lyophilised hemisulfate salt of 5,10-methylene-(6R)-tetrahydrofolic acid free acid (about 10% w/w) at the 0 min time-point. Both measurements were performed right after each other. At all other time-points results were at approximately 80% w/w free acid content for both storage conditions. This indicates a systematic error of the measurement for the two higher free acid content results. Aside from those two results the free acid content remains more or less unchanged during the study.

The Purity at room temperature remains within the limit of "not less than 95% Area" up to 200 minutes (3.3 h). When stored refrigerated the sample solution is much more stable and the purity is within the >95 area % for up to 24 hours.

However, related compound DHFA and sum of related compounds should be considered as stability indicating factors as well. At room temperature DHFA remains within limit up to 100 min. At this time-point the sum of related compounds is slightly outside of the applied limit. In the sample solution stored at 2-8° C. DHFA and the sum of related compounds were within the limit up to 200 min. A combination of cold storage and short equilibration time at room temperature (less than 50 min) of the lyophilised hemisulfate salt of 5,10-methylene-(6R)-tetrahydrofolic acid sample solution is justified by the data obtained in this study.

Example 4-1

Stability studies were performed as in the examples above. The conditions for the studies are provided with each data set provided. Some of the data in this example is from previous examples herein, but are reproduced here to provide some kind of a side-by-side nature of the presentation of the results.

Some data provided below are not completely side-by-side. However, noted is that one of ordinary skill in the art knows that the lower the temperature for stability studies, the more stable a product is generally with near certainty. As such, one knows the general effect of temperature and can therefore easily understand the probative value of a comparison where the temperatures may not have been completely equal. This trend is also clearly evident in the data sets provided below as will be explained below once the data is provided.

In the present case, one skilled in the art looking at the stability data of the sulfate salt of 5,10-methylene-(6R)-tetrahydrofolic acid as disclosed in the application where the first 15 months of the stability were tested at −20° C., would know that at higher temperatures the results would look even less favorable for said sulfate salt compound. This means that any improvement demonstrated with the hemisulfate salt where the temperatures are higher should have been even higher if the comparison would have been done truly side-by-side. Moreover, in the present case, even if one would completely ignore the beneficial temperature effect for the comparison data of the sulfate salt of 5,10-methylene-(6R)-tetrahydrofolic acid, the data sets still clearly demonstrate significant improvement with the hemisulfate salt of 5,10-methylene-(6R)-tetrahydrofolic acid.

As such, the results provided in this example certainly and consistently demonstrate significantly improved stability of the hemisulfate salt of 5,10-methylene-(6R)-tetrahydrofolic acid over the sulfate salt of 5,10-methylene-(6R)-tetrahydrofolic acid.

A) Stability at −20° C.

The data at −20° C. on the sulfate salt in comparison to data generated by measurements on three batches of the hemisulfate salt is provided in graph form in FIG. 6.

These results already demonstrate some improvement even at this low temperature where the stabilities of all compounds are quite good, i.e., there is an indication of an improved stability of the hemisulfate salt over the sulfate salt of the compound.

However, the improvement is even clearer when looking at the measurement of the stability marker 10-formyltetrahydrofolic acid. One can clearly see the difference between the two compounds, i.e., that the hemisulfate salt of 5,10-methylene-(6R)-tetrahydrofolic acid shows in all measurements over time a significantly lower content of the stability marker. For the hemisulfate salt of 5,10-methylene-(6R)-tetrahydrofolic acid the stability marker also keeps a steady state on a very low basis, whereas the 2 values for the sulfate salt show a remarkable increase in the stability marker over time. See the graphically provided results in FIG. 7.

B) Stability at 5° C. resp. 25° C.

Even clearer is the showing of significantly improved results with the data set provided in FIG. 8 at various temperatures.

Noted is that the data on the stability for the sulfate salt of 5,10-methylene-(6R)-tetrahydrofolic acid at 5° C. and respectively 25° C. is in an embodiment where the first 15 month of the stability was done at −20° C. As explained above, one would know that this favors improved results for the sulfate salt compound, and that a comparison at higher temperatures throughout the entire time for the sulfate salt compound should have led to even higher improvements for the hemisulfate salt of the compound over the sulfate salt comparison.

Additionally, noted is that the data set in FIG. 8 confirms that the temperature increase in the present case, as one would expect, leads to lower stability. In this regard, see that for the first 15 months for the sulfate salt, where the temperature is −20° C., the measured purity decreases much less significantly than during the next few months where the temperature is increased for the same compound, e.g., to 5° C. and 25° C., respectively. This clearly indicates that the temperature increase leads to faster degradation, and that thereby any comparison where the temperature favors stability for the sulfate salt compound should have indicated an even higher improvement for the hemisulfate salt if the tests were done completely side-by-side for the entire duration of the tests.

The data in the graph of FIG. 8 clearly demonstrate that the hemisulfate salt of 5,10-methylene-(6R)-tetrahydrofolic acid stored at 25° C./60% rh is far more stable over time than the sulfate salt. Even if one would ignore the lower temperature for the first 15 months for the sulfate salt, at the same 25° C./60% rh conditions from month 15 on (i.e., in the side-by-side part of the comparison with identical conditions—see months 10 to 21), the decrease in purity is significantly more than for any of the hemisulfate batches.

Moreover, the hemisulfate salt of 5,10-methylene-(6R)-tetrahydrofolic acid is even more stable when stored at 25° C./60% rh than the sulfate salt which is stored at a lower 5° C. after 15 months (and here too ignoring that the first 15 months of storage of the sulfate were taken at −20° C.).

The significantly improved results would be clearly expected to be even higher in a completely side-by-side comparison throughout the entire time of the study.

The same conclusion can be also drawn from the graph in FIG. 9 where the content of the stability marker 10-formyltetrahydrofolic acid is shown. There too one can clearly see that the hemisulfate salt of 5,10-methylene-(6R)-tetrahydrofolic acid shows in all measurements over time a lower content of the stability marker. Also noted is that the stability marker for the hemisulfate salt of 5,10-methylene-(6R)-tetrahydrofolic acid stored at 25° C. is lower than the stability marker for the sulfate compound stored, even where storages is for the first 15 months at −20° C. and then at a still lower 5° C.

The graphically provided data sets for this example are also provided in tabulated form along with additional data in FIG. 10 clearly and consistently with the above demonstrating significant improvement for the hemisulfate salt. See, e.g., the data in the table at even higher temperatures of +40° C. and a relative humidity of 75% where the hemisulfate salt still shows an excellent stability. Thus, the data demonstrate that the improved stability holds up through various unfavorable conditions for extended periods of time for the hemisulfate salt, which is not the situation for the sulfate salt as evidenced by the herein provided data.

In sum, provided herein are a broad set of stability data generated on 3 different batches of the hemisulfate salt of 5,10-methylenetetrahydrofolic acid, which is compared to the sulfate salt of the compound. These data clearly demonstrate superior stability of the hemisulfate salt. Moreover, even at elevated temperatures of +40° C. and a relative humidity of 75% the hemisulfate salt shows an excellent stability.

Based on the data above, it is concluded that the hemisulfate salt of 5,10-methylene-(6R)-tetrahydrofolic acid is remarkably more stable than the sulfate salt compound, and that such is a significantly improved stability could not have been expected from anything in the prior art, including from the knowledge of the existence of the sulfate salt of the compound, e.g., from Mueller et al. (U.S. Pat. No. 5,300,505)

BRIEF DESCRIPTION OF THE DRAWINGS

FIG. 2 (*b*): X-Ray Powder Diffractogram of the hemisulfate salt of (6R)-5,10-CH$_2$-THF (Type 1) recorded in the transmission mode;

FIG. 2 (*c*): Comparison of X-ray diffraction pattern of the hemisulfate salt of (6R)-5,10-CH$_2$-THF (Type 1) recorded in transmission mode (upper curve A) with a recording of the same compound recorded in reflection mode (lower curve B);

FIG. 2 (*d*): Comparison of X-ray diffraction pattern of the hemisulfate salt of (6R)-5,10-CH$_2$-THF (Type 1) (upper curve A) with an X-ray diffraction pattern of the sulfate salt of (6R)-5,10-CH$_2$-THF (lower curve B) recorded in the transmission mode.

FIG. 10: Illustrates tabulated data for Example 4-1.

In sum, disclosed are the following aspects:

Aspect 1: A hemisulfate salt of 5,10-methylene-(6R)-tetrahydrofolic acid.

Aspect 2: The hemisulfate salt according to aspect 1, which has been dissolved in water or in a liquid pharmaceutically acceptable vehicle, wherein the resultant solution has a pH of between 5 and 10.5.

Aspect 3: The hemisulfate salt of aspect 1, which is anhydrous; or which is in crystalline form; or which is in amorphous form.

Aspect 4: A lyophilisate comprising the hemisulfate salt of aspect 2 or made therefrom.

Figure 1:
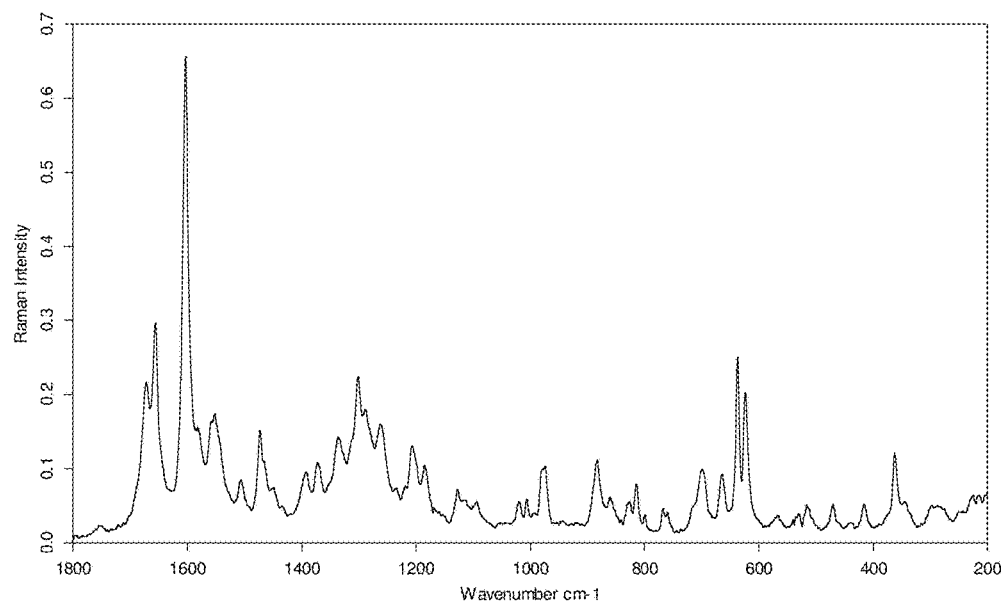
FIG. 1: Raman spectrum of the hemisulfate salt of (6R)-5,10-CH$_2$-THF (Type 1), recorded using a nominal laser power level of 300 mW and 64 scans.
Figure 2:
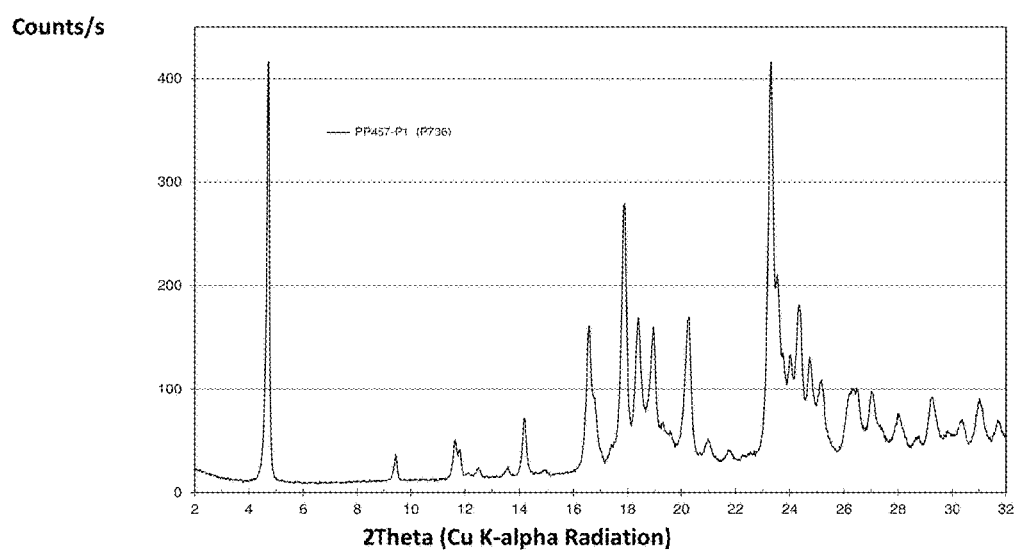
FIG. 2 (*a*): X-Ray Powder Diffractogram of the hemisulfate salt of (6R)-5,10-CH$_2$-THF (Type 1) recorded in the reflection mode.
Figure 2:
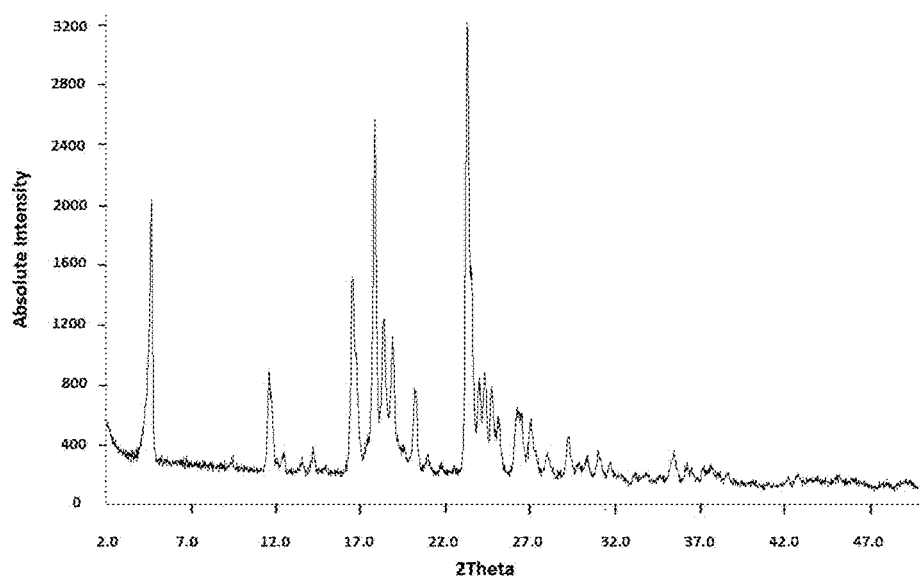
Figure 2:
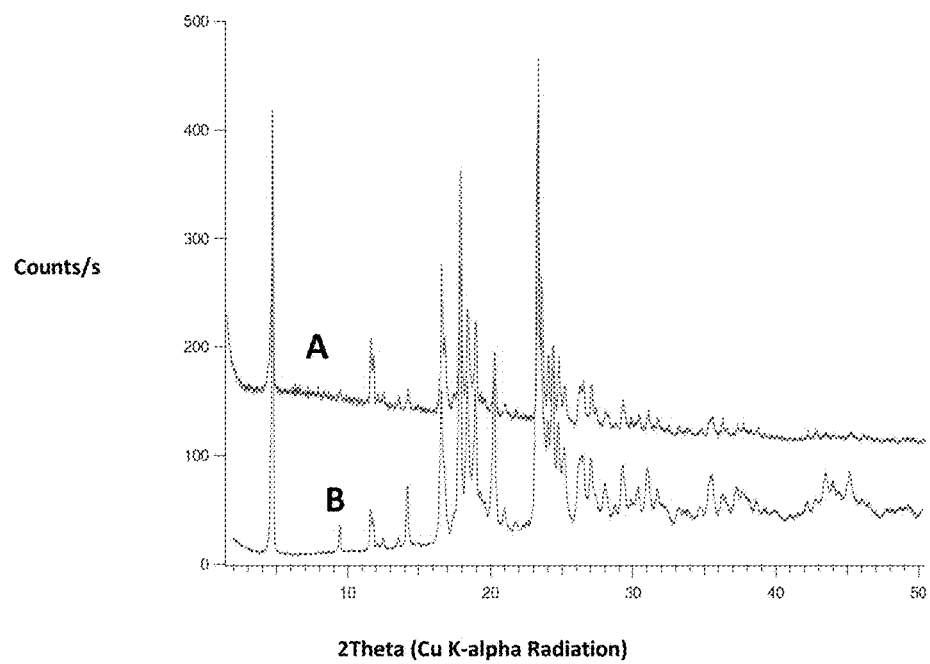
Figure 2:
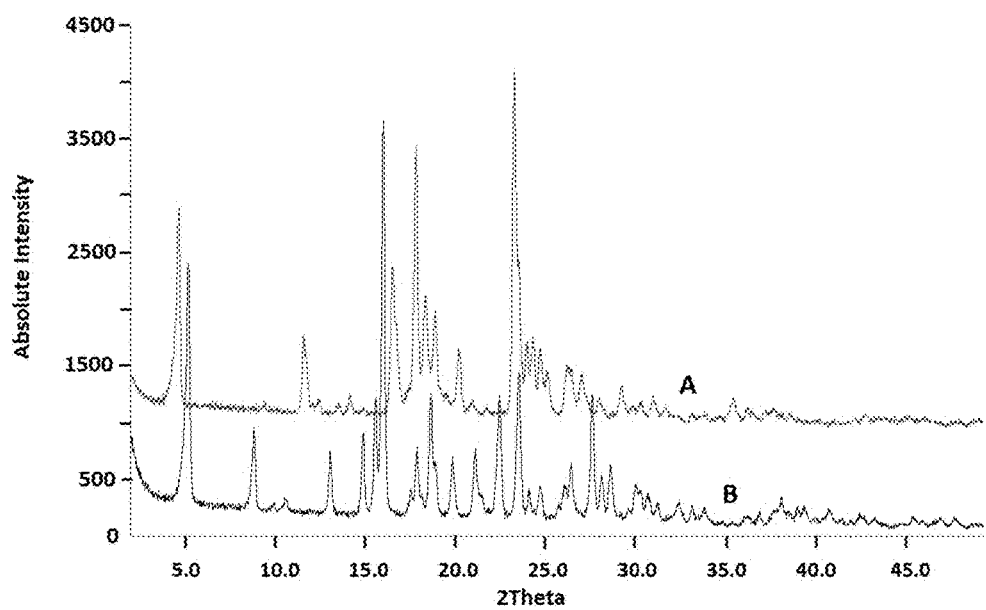
Figure 3:
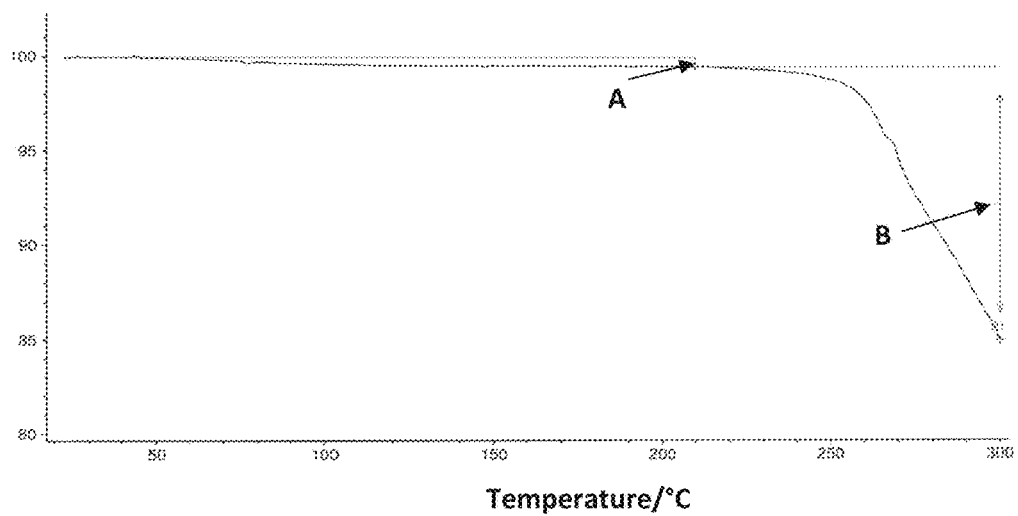
FIG. 3: TG-FTIR thermogram of the hemisulfate salt of (6R)-5,10-CH$_2$-THF (Type 1). "A" indicates a change in mass of −0.5% (due to loss of water) and "B" indicates a change in mass of −14.53% (due to decomposition)
Figure 4:
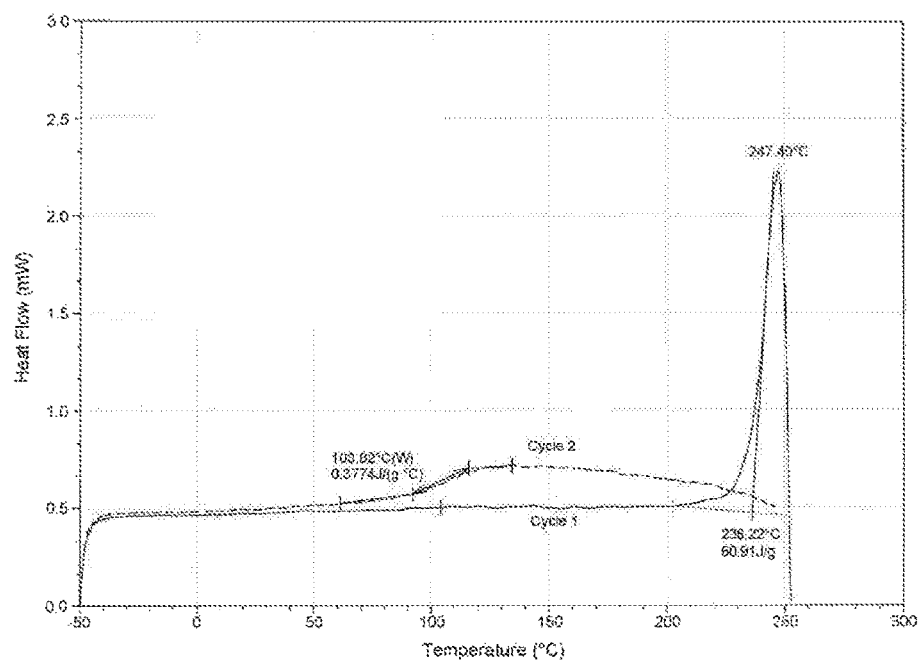
FIG. 4: DSC thermogram of the hemisulfate salt of (6R)-5,10-CH$_2$-THF (Type 1; first scan: solid line; second scan (after quench cooling): dashed line).
Figure 5:
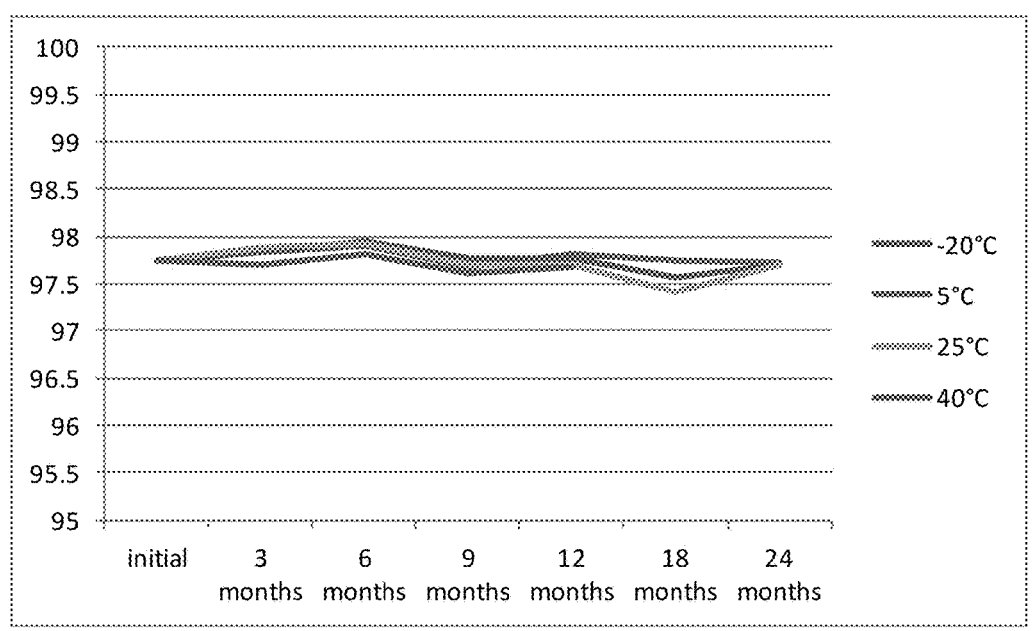
FIG. 5: Shows HPLC purity results of the lyophilised hemisulfate salt of 5,10-methylene-(6R)-tetrahydrofolic acid through 24 months of testing at all tested conditions.
Figure 6:
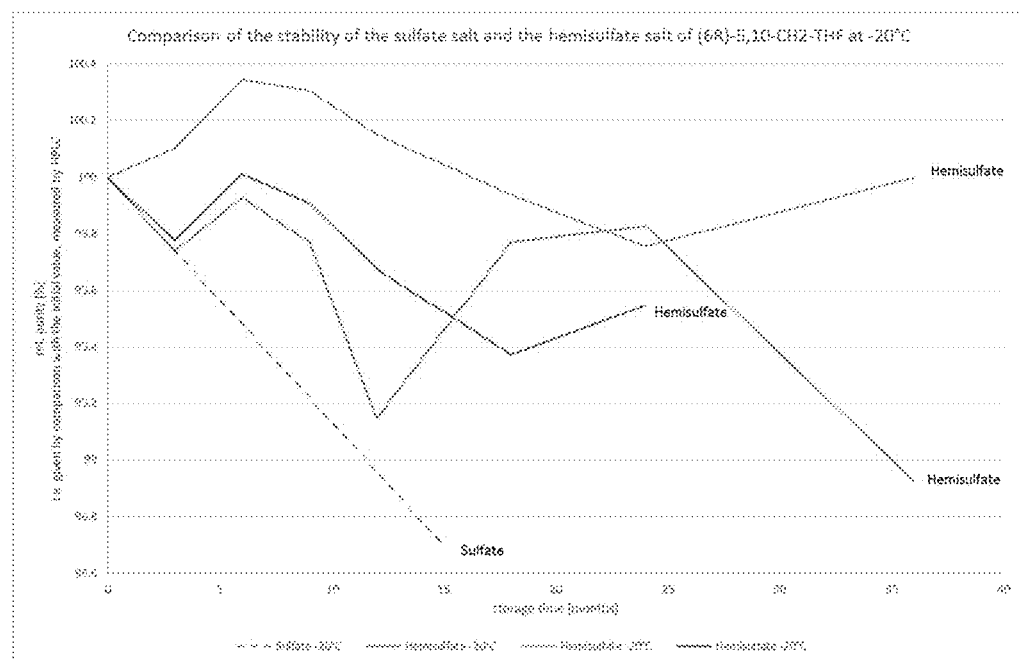
FIG. 6: Illustrates stability data at −20° C. of the sulfate salt in comparison to data generated by measurements on three batches of the hemisulfate salt provided.
Figure 7:
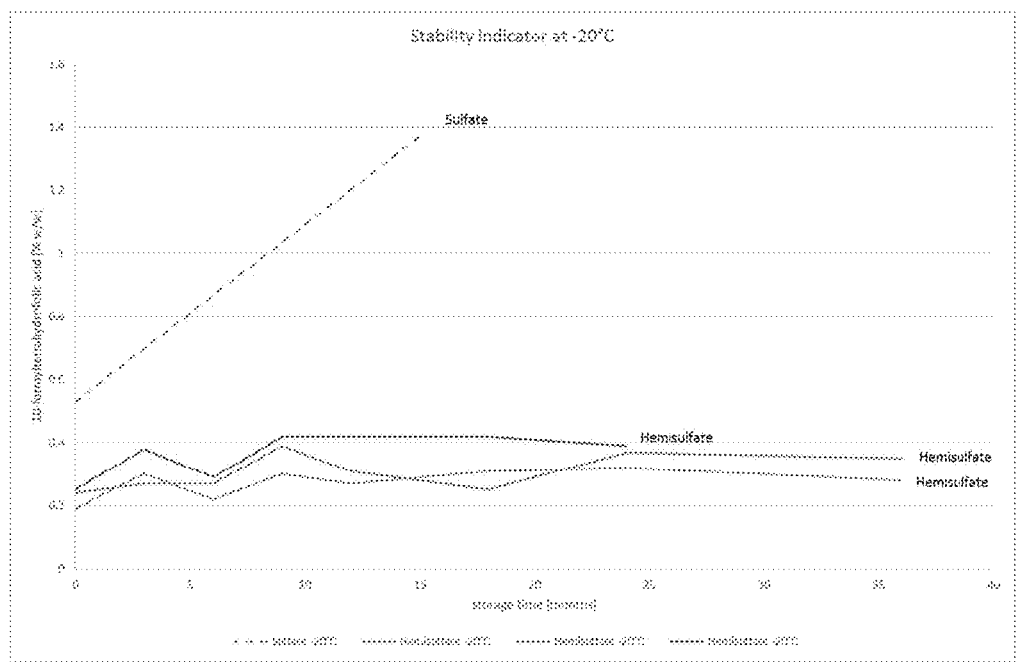
FIG. 7: Illustrates stability marker results graphically at −20° C. of the sulfate salt in comparison to data generated by measurements on three batches of the hemisulfate salt.
Figure 8:
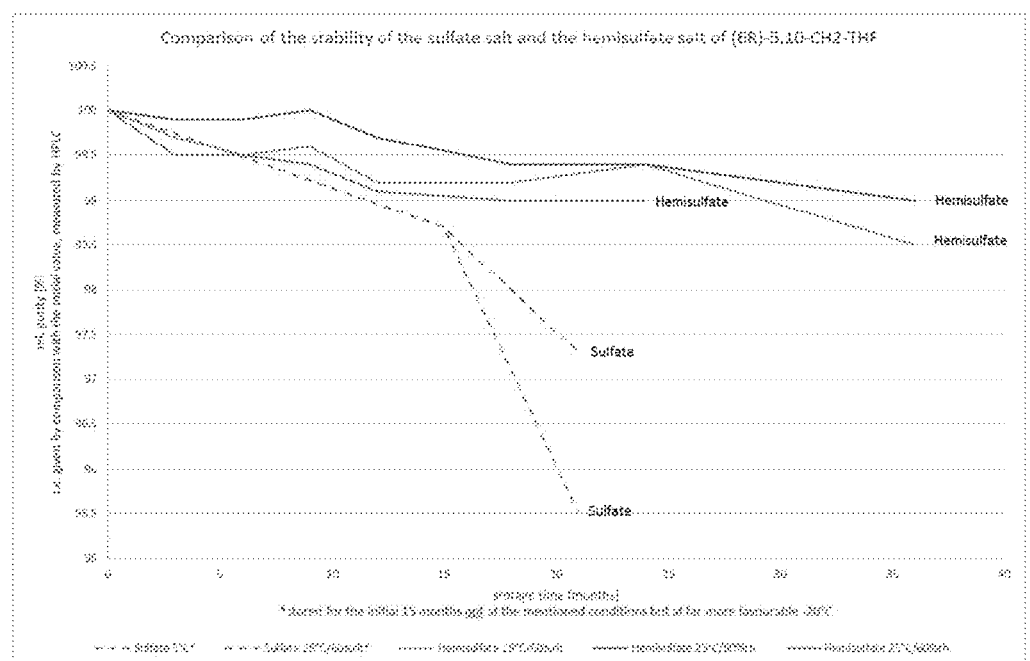
FIG. 8: Illustrates the showing of improved stability data at various temperatures by measurements on three batches of the hemisulfate salt in comparison to the sulfate salt.
Figure 9:
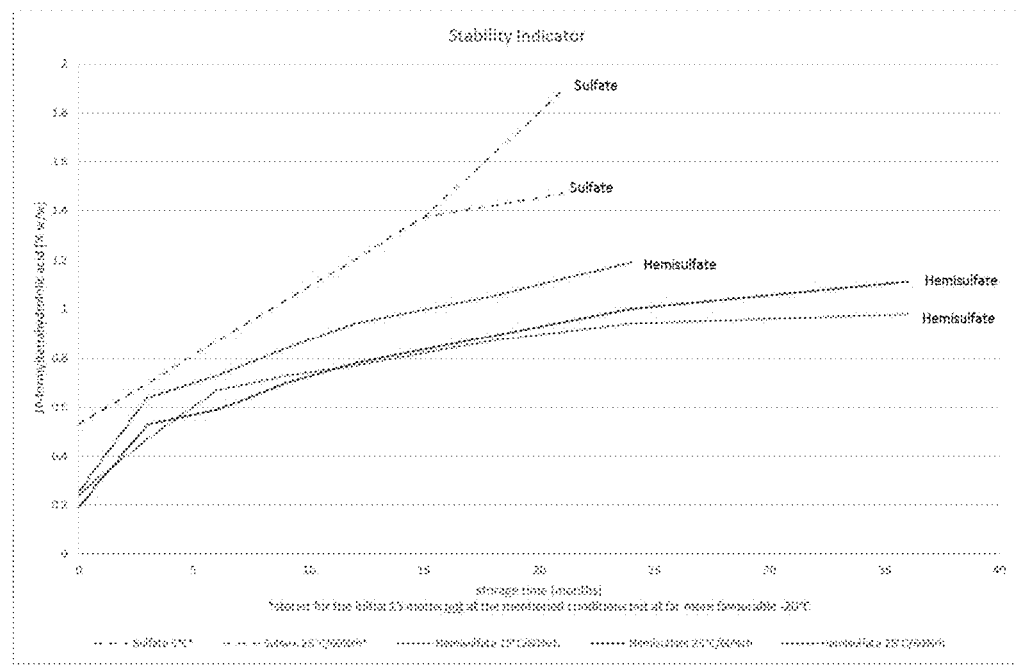
FIG. 9: Illustrates stability marker results graphically for the showing of improved stability at various temperatures by measurements on three batches of the hemisulfate salt in comparison to the sulfate salt.

Aspect 5: The hemisulfate salt of aspect 3, which is in crystalline form, wherein the hemisulfate salt has one or more X-ray pattern peak positions at an angle of diffraction 2 theta of 4.7°, 17.9°, and 23.3° expressed in 2θ±0.2° 2θ CuKα radiation, reflection; or wherein the hemisulfate salt has a FT-Raman spectrum containing one or more peaks at wavenumbers, expressed in ±2 cm$^{-1}$, of 1672, 1656, 1603, 1553, 1474, 1301, 637, 624 and 363; or wherein the hemisulfate salt has a FT-Raman spectrum substantially in accordance with FIG. 1; or wherein the hemisulfate salt has an X-ray powder diffraction pattern substantially in accordance with FIG. 2(*a*); or wherein the hemisulfate salt has an X-ray powder diffraction pattern substantially in accordance with FIG. 2(*b*).

Aspect 6: The hemisulfate salt of aspect 1, having a stereoisomeric purity of greater than 99%; preferably having a stereoisomeric purity of greater than 99.5%; or having a chemical purity of greater than 99%; preferably having a chemical purity of greater than 99.5%.

Aspect 7: A pharmaceutical composition comprising a hemisulfate salt of aspect 1 and a pharmaceutically acceptable carrier.

Aspect 8: A pharmaceutical composition of aspect 7 further comprising a buffer, which buffer is preferably citrate, phosphate, acetate, TRIS, N-tris(hydroxymethyl)methyl-2-aminoethanesulfonic acid (TES), 3-(N-morpholino) propanesulfonic acid (MOPS), N,N-bis(2-hydroxyethyl)-2-aminoethanesulfonic acid (BES), MES, MOPSO, HEPES, succinate, carbonate, ammonium, mono-, di- or tri-alkylammonium, mono-, di- or tri-hydroxylalkylammonium, maleate, glutamate, borate, lactate or a combination thereof, and more preferably the buffer is citrate.

Aspect 9: The lyophilisate of aspect 4, wherein the molar ratio between the (6R)-5,10-CH$_2$-THF and sulfuric acid moieties is from about 1:1 to about 2:1.

Aspect 10: A process for preparing a lyophilized product comprising the step of lyophilizing a pharmaceutical composition comprising a hemisulfate salt of aspect 1 and a pharmaceutically acceptable carrier.

Aspect 11: A process for preparing a liquid pharmaceutical composition from the lyophilisate of aspect 4 comprising dissolving the lyophilized pharmaceutical composition in water and/or a liquid pharmaceutically acceptable vehicle.

Aspect 12: A method for treating breast cancer, esophageal cancer, gastric cancer, gall bladder cancer, bile duct cancer, colon cancer, rectal cancer, colorectal cancer (CRC) including metastatic CRC, osteosarcoma, liver cancer, pancreatic cancer, ovarian cancer, head and neck cancer, mesotheolioma cancer, stomach cancer, bowel cancer, or lung cancer (specifically adenocarcinoma), comprising administering an effective amount of a pharmaceutical composition to a patient in need thereof, which composition comprises:
A) a hemisulfate salt of 5,10-methylene-(6R)-tetrahydrofolic acid according to aspect 1,
B) a lyophilisate comprising the hemisulfate salt of 5,10-methylene-(6R)-tetrahydrofolic acid or made therefrom,
C) a reconstituted solution from the lyophilisate of B), which has been reconstituted by water or a liquid pharmaceutically acceptable vehicle;
and which method preferably includes also administering to said patient an effective amount of a further pharmaceutically active compound, e.g., a cytotoxic compound, for example, 5-fluorouracil, pemetrexed, high-dose methotrexate, oxaliplatin, avastin, etc., which further active compound is suitable for the treatment of said breast cancer, esophageal cancer, gastric cancer, gall bladder cancer, bile duct cancer, colon cancer, rectal cancer, colorectal cancer (CRC) including metastatic CRC, osteosarcoma, liver cancer, pancreatic cancer, ovarian cancer, head and neck cancer, mesotheolioma cancer, stomach cancer, bowel cancer, or lung cancer (specifically adenocarcinoma). One could use the pharmaceutical composition recited in this method for the treatment of indications for which Levoleucovorin (or Leucovorin) is used. For example, the 5-FU based chemotherapy is based on the inhibition of TS because of the very special, unnatural, ternary complex.

Aspect 13: A product, which is
i) a lyophilisate comprising the sulfate salt of 5,10-methylene-(6R)-tetrahydrofolic acid or made therefrom without the presence of citrate, wherein preferably the lyophilisate comprises the 5,10-methylene-(6R)-tetrahydrofolic acid and sulfate and optionally sodium ions without the presence of citrate,
ii) a lyophilisate comprising 5,10-methylene-(6R)-tetrahydrofolic acid without the presence of citrate,
iii) a reconstituted solution from the lyophilisate of i) or ii), which has been reconstituted by water or a liquid pharmaceutically acceptable vehicle.

Aspect 14: A method for treating breast cancer, esophageal cancer, gastric cancer, gall bladder cancer, bile duct cancer, colon cancer, rectal cancer, colorectal cancer (CRC) including metastatic CRC, osteosarcoma, liver cancer, pancreatic cancer, ovarian cancer, head and neck cancer, mesotheolioma cancer, stomach cancer, bowel cancer, or lung cancer (specifically adenocarcinoma), comprising administering an effective amount of a pharmaceutical composition to a patient in need thereof, which composition comprises a product according to aspect 13; and which method preferably includes also administering to said patient an effective amount of a further pharmaceutically active compound, e.g., a cytotoxic compound, for example, 5-fluorouracil, pemetrexed, high-dose methotrexate, oxaliplatin, avastin, etc., which further active compound is suitable for the treatment of said breast cancer, esophageal cancer, gastric cancer, gall bladder cancer, bile duct cancer, colon cancer, rectal cancer, colorectal cancer (CRC) including metastatic CRC, osteosarcoma, liver cancer, pancreatic cancer, ovarian cancer, head and neck cancer, mesotheolioma cancer, stomach cancer, bowel cancer, or lung cancer (specifically adenocarcinoma). One could use the pharmaceutical composition recited in this method for the treatment of indications for which Levoleucovorin (or Leucovorin) is used. For example, the 5-FU based chemotherapy is based on the inhibition of TS because of the very special, unnatural, ternary complex.

Aspect 15: A reconstituted solution from a lyophilisate according to aspect 4, which has been reconstituted by water or a liquid pharmaceutically acceptable vehicle.

Aspect 16: A reconstituted solution according to aspect 15, wherein the molar ratio between the (6R)-5,10-$CH_2$-THF and $H_2SO_4$ moieties is from about 1:1 to about 2:1, preferably about 2:1.

Aspect 17: A product, which is a lyophilized formulation A, B, C, D or E, which
A) is prepared from a hemisulfate salt of 5,10-methylene-(6R)-tetrahydrofolic acid,
B) comprises 5,10-methylene-(6R)-tetrahydrofolic acid and/or 5,10-methylene-(6R)-tetrahydrofolate resulting from a hemisulfate salt of 5,10-methylene-(6R)-tetrahydrofolic acid,
C) comprises about two moles of 5,10-methylene-(6M-tetrahydrofolic acid and/or 5,10-methylene-(6R)-tetrahydrofolate to one mole of sulfate ions,
D) comprises about 1 mole of 5,10-methylene-(6R)-tetrahydrofolic acid and/or 5,10-methylene-(6R)-tetrahydrofolate to one mole of sulfate ions without the presence of citrate,
E) comprises 5,10-methylene-(6R)-tetrahydrofolic acid and/or 5,10-methylene-(6R)-tetrahydrofolate having a chemical purity of greater than 99%, more preferably 99.5%, or even higher, e.g., 99.6, 99.7, 99.8 or 99.9% or above, e.g., 100, and sulfate with the presence of citrate or without the presence of citrate; or
which is a stable pharmaceutical composition X or Y comprising 5,10-methylene-(6R)-tetrahydrofolic acid, which composition comprises
X) a lyophilised hemisulfate salt of 5,10-methylene-(6R)-tetrahydrofolic acid, which has such stability that the composition maintains greater than or equal to 95%, preferably between 97-98%, and more preferably at about 99%, of purity of the 5,10-methylene-(6R)-tetrahydrofolic acid for at least 24 months, preferably for at least 36 months, and more preferably for at least 48 months at +25° C./60% relative humidity; or for at least 12 months at +40° C./75% relative humidity, or for at least 24 months, preferably at least 36 months, and more preferably for at least 48 months at +5° C., or for at least 24 months, preferably at least 36 months at −20° C.; or
Y) a reconstituted lyophilised hemisulfate salt of 5,10-methylene-(6R)-tetrahydrofolic acid, which has such stability that the composition maintains greater than or equal to 95%, preferably between 95-96%, and more preferably at about 97%, of purity of the 5,10-methylene-(6R)-tetrahydrofolic acid for at least 200 minutes, preferably 6 hours, and more preferably 11 or 12 hours at 2-8° C., or for at least 2 hours, and more preferably for at least 200 minutes at room temperature.

Aspect 18: A method for treating breast cancer, esophageal cancer, gastric cancer, gall bladder cancer, bile duct cancer, colon cancer, rectal cancer, colorectal cancer (CRC) including metastatic CRC, osteosarcoma, liver cancer, pancreatic cancer, ovarian cancer, head and neck cancer, mesotheolioma cancer, stomach cancer, bowel cancer, or lung cancer (specifically adenocarcinoma), comprising administering an effective amount of a pharmaceutical composition to a patient in need thereof, which composition comprises a product according to aspect 17; and which method preferably includes also administering to said patient an effective amount of a further pharmaceutically active compound, e.g., a cytotoxic compound, for example, 5-fluorouracil, pemetrexed, high-dose methotrexate, oxaliplatin, avastin, etc., which further active compound is suitable for the treatment of said breast cancer, esophageal cancer, gastric cancer, gall bladder cancer, bile duct cancer, colon cancer, rectal cancer, colorectal cancer (CRC) including metastatic CRC, osteosarcoma, liver cancer, pancreatic cancer, ovarian cancer, head and neck cancer, mesotheolioma cancer, stomach cancer, bowel cancer, or lung cancer (specifically adenocarcinoma). One could use the pharmaceutical composition recited in this method for the treatment of indications for which Levoleucovorin (or Leucovorin) is used. For example, the 5-FU based chemotherapy is based on the inhibition of TS because of the very special, unnatural, ternary complex.

Aspect 19: A method for methotrexate therapy, comprising administering methotrexate to a subject in need thereof, and additionally administering
A) a hemisulfate salt of 5,10-methylene-(6R)-tetrahydrofolic acid according to aspect 1,
B) a lyophilisate comprising the hemisulfate salt of 5,10-methylene-(6R)-tetrahydrofolic acid or made therefrom,
C) a reconstituted solution from the lyophilisate of B), which has been reconstituted by water or a liquid pharmaceutically acceptable vehicle.

Aspect 20: In a method for methotrexate therapy, wherein the improvement comprises administering
A) a hemisulfate salt of 5,10-methylene-(6R)-tetrahydrofolic acid according to aspect 1,
B) a lyophilisate comprising the hemisulfate salt of 5,10-methylene-(6R)-tetrahydrofolic acid or made therefrom,
C) a reconstituted solution from the lyophilisate of B), which has been reconstituted by water or a liquid pharmaceutically acceptable vehicle.

Aspect 21: A method for methotrexate therapy, comprising administering methotrexate to a subject in need thereof, and additionally administering a product of aspect 13.

Methotrexate therapy is typically used in the treatment of various types of cancers as well as various autoimmune diseases. Cancers for which methotrexate therapy is used include skin cancers, breast cancer, head and neck cancer, e.g., epidermoid cancers of the head and neck, lung cancer, particularly squamous cell and small cell types, leukemia, e.g., acute lymphoblastic leukemia (ALL), lymphoma, e.g., non-Hodgkin's lymphoma (NHL) and central nervous system (CNS) lymphoma, mycosis fungoides (cutaneous T-cell lymphoma), colon cancer, colorectal cancer, rectal cancer, stomach cancer, esophageal cancer, choriocarcinoma, chorioadenoma, gestational trophoblastic disease, osteosarcoma, nonleukemic meningeal cancer, soft tissue sarcoma (desmoid tumors, aggressive fibromatosis) and bladder cancer. Methotrexate therapy is also used in the treatment of psoriasis, rheumatoid arthritis, Crohn's disease, juvenile dermatomyositis, psoriatic arthritis, lupus, sarcoidosis, eczema, vasculitis, dermatomyositis/polymyositis, ectopic pregnancy, systemic lupus erythematosus, and Takayasu arteritis, and for prevention of graft-versus-host disease.

The use of the compounds of the invention in methotrexate therapy can rather be considered a rescue cancer therapy. In this case, there isn't the same inhibitory ternary complex that includes, for example, the 5-FU molecule, but instead is the "normal ternary complex" that includes uracil instead of 5-FU, and which instead speeds up the "normal" formation of thymidine and DNA, and both in the normal cells and in the tumours.

From the preceding description, one skilled in the art in this field can read the elements of the invention without problems, and, without departing from the basic idea and from the scope of the invention, can make modifications and additions and can thereby adapt the invention to differing needs and conditions.

The entire disclosures of all the patent applications, patents and publications which are cited in this text are included jointly by reference.

The invention claimed is:

1. A hemisulfate salt of 5,10-methylene-(6R)-tetrahydrofolic acid.

2. The hemisulfate salt according to claim 1, which has been dissolved in water or in a liquid pharmaceutically acceptable vehicle, wherein the resultant solution has a pH of between 5 and 10.5.

3. The hemisulfate salt of claim 1, which is anhydrous; or which is in crystalline form; or which is in amorphous form.

4. A lyophilisate comprising the hemisulfate salt of claim 2 or made therefrom.

5. The hemisulfate salt of claim 3, which is in crystalline form, wherein the hemisulfate salt has one or more X-ray pattern peak positions at an angle of diffraction 2 theta of 4.7°, 17.9°, and 23.3° expressed in 2θ±0.2° 2θ CuKα radiation, reflection; or wherein the hemisulfate salt has a FT-Raman spectrum containing one or more peaks at wavenumbers, expressed in ±2 cm$^{-1}$, of 1672, 1656, 1603, 1553, 1474, 1301, 637, 624 and 363; or wherein the hemisulfate salt has a FT-Raman spectrum substantially in accordance with FIG. 1; or wherein the hemisulfate salt has an X-ray powder diffraction pattern substantially in accordance with FIG. 2(a); or wherein the hemisulfate salt has an X-ray powder diffraction pattern substantially in accordance with FIG. 2(b).

6. The hemisulfate salt of claim 1, having a stereoisomeric purity of greater than 99%; or having a chemical purity of greater than 99%.

7. A pharmaceutical composition comprising a hemisulfate salt of claim 1 and a pharmaceutically acceptable carrier.

8. A pharmaceutical composition of claim 7 further comprising a buffer.

9. The lyophilisate of claim 4, wherein the molar ratio between the (6R)-5,10-CH$_2$-THF and sulfuric acid moieties is from about 1:1 to about 2:1.

10. A process for preparing a lyophilized product comprising the step of lyophilizing a pharmaceutical composition comprising a hemisulfate salt of claim 1 and a pharmaceutically acceptable carrier.

11. A process for preparing a liquid pharmaceutical composition from the lyophilisate of claim 4 comprising dissolving the lyophilized pharmaceutical composition in water and/or a liquid pharmaceutically acceptable vehicle.

12. A product, which is
i) a lyophilisate comprising the sulfate salt of 5,10-methylene-(6R)-tetrahydrofolic acid or made therefrom without the presence of citrate,
ii) a lyophilisate comprising 5,10-methylene-(6R)-tetrahydrofolic acid without the presence of citrate, or
iii) a reconstituted solution from the lyophilisate of i) or ii), which has been reconstituted by water or a liquid pharmaceutically acceptable vehicle.

13. A reconstituted solution from a lyophilisate according to claim 4, which has been reconstituted by water or a liquid pharmaceutically acceptable vehicle.

14. A reconstituted solution according to claim 13, wherein the molar ratio between the (6R)-5,10-CH$_2$-THF and H$_2$SO$_4$ moieties is from about 1:1 to about 2:1.

15. A product, which is a lyophilized formulation A, B, C, D or E, which
- A) is prepared from a hemisulfate salt of 5,10-methylene-(6R)-tetrahydrofolic acid,
- B) comprises 5,10-methylene-(6R)-tetrahydrofolic acid and/or 5,10-methylene-(6R)-tetrahydrofolate resulting from a hemisulfate salt of 5,10-methylene-(6R)-tetrahydrofolic acid,
- C) comprises about two moles of 5,10-methylene-(6R)-tetrahydrofolic acid and/or 5,10-methylene-(6R)-tetrahydrofolate to one mole of sulfate ions,
- D) comprises about 1 mole of 5,10-methylene-(6R)-tetrahydrofolic acid and/or 5,10-methylene-(6R)-tetrahydrofolate to one mole of sulfate ions without the presence of citrate, or
- E) comprises 5,10-methylene-(6R)-tetrahydrofolic acid and/or 5,10-methylene-(6R)-tetrahydrofolate having a chemical purity of greater than 99%, and sulfate with the presence of citrate or without the presence of citrate; or which is a stable pharmaceutical composition X or Y comprising
- X) a lyophilised hemisulfate salt of 5,10-methylene-(6R)-tetrahydrofolic acid, which has such stability that the composition maintains greater than or equal to 95% of purity of the 5,10-methylene-(6R)-tetrahydrofolic acid for at least 24 months at +25° C./60% relative humidity; or for at least 12 months at +40° C./75% relative humidity, or for at least 24 months at +5° C., or for at least 24 months at −20° C.; or
- Y) a reconstituted lyophilised hemisulfate salt of 5,10-methylene-(6R)-tetrahydrofolic acid, which has such stability that the composition maintains greater than or equal to 95% of purity of the 5,10-methylene-(6R)-tetrahydrofolic acid for at least 200 minutes at 2-8° C., or for at least 2 hours at room temperature.

16. The hemisulfate salt of claim 1, having a stereoisomeric purity of greater than 99%; or having a chemical purity of greater than 99%.

17. A pharmaceutical composition of claim 7 further comprising a buffer, which buffer is citrate, phosphate, acetate, TRIS, N-tris(hydroxymethyl) methyl-2-aminoethanesulfonic acid (TES), 3-(N-morpholino) propanesulfonic acid (MOPS), N,N-bis(2-hydroxyethyl)-2-aminoethanesulfonic acid (BES), MES, MOPSO, HEPES, succinate, carbonate, ammonium, mono-, di- or tri-alkylammonium, mono-, di- or tri-hydroxylalkylammonium, maleate, glutamate, borate, lactate or a combination thereof.

18. A pharmaceutical composition of claim 7 further comprising a buffer, which buffer is citrate.

19. A product according to claim 12, which is product i), wherein the lyophilisate comprises the 5,10-methylene-(6R)-tetrahydrofolic acid and sulfate and optionally sodium ions without the presence of citrate.

20. A reconstituted solution according to claim 13, wherein the molar ratio between the (6R)-5,10-CH$_2$-THF and H$_2$SO$_4$ moieties is about 2:1.

21. A product according to claim 15, which is a lyophilized formulation E, which
- E) comprises 5,10-methylene-(6R)-tetrahydrofolic acid and/or 5,10-methylene-(6R)-tetrahydrofolate having a chemical purity of greater than 99.5%, and sulfate with the presence of citrate or without the presence of citrate.

22. A product according to claim 15, which is a stable pharmaceutical composition X comprising
- X) a lyophilised hemisulfate salt of 5,10-methylene-(6R)-tetrahydrofolic acid, which has such stability that the composition maintains about 99% of purity of the 5,10-methylene-(6R)-tetrahydrofolic acid for at least 48 months at +25° C./60% relative humidity; or for at least 12 months at +40° C./75% relative humidity, or for at least 48 months at +5° C., or for at least 36 months at −20° C.

23. A product according to claim 15, which is a stable pharmaceutical composition Y comprising
- Y) a reconstituted lyophilised hemisulfate salt of 5,10-methylene-(6R)-tetrahydrofolic acid, which has such stability that the composition maintains about 97% of purity of the 5,10-methylene-(6R)-tetrahydrofolic acid for 11 or 12 hours at 2-8° C., or for at least 200 minutes at room temperature.

24. A product according to claim 12, which is
- i) a lyophilisate comprising the sulfate salt of 5,10-methylene-(6R)-tetrahydrofolic acid or made therefrom without the presence of citrate.

25. A product according to claim 12, which is
- ii) a lyophilisate comprising 5,10-methylene-(6R)-tetrahydrofolic acid without the presence of citrate.

26. A product according to claim 12, which is
- iii) a reconstituted solution from the lyophilisate of i) or ii), which has been reconstituted by water or a liquid pharmaceutically acceptable vehicle.

27. A product according to claim 15, which is a lyophilized formulation A, which
- A) is prepared from a hemisulfate salt of 5,10-methylene-(6R)-tetrahydrofolic acid.

28. A product according to claim 15, which is a lyophilized formulation B, which
- B) comprises 5,10-methylene-(6R)-tetrahydrofolic acid and/or 5,10-methylene-(6R)-tetrahydrofolate resulting from a hemisulfate salt of 5,10-methylene-(6R)-tetrahydrofolic acid.

29. A product according to claim 15, which is a lyophilized formulation C, which
- C) comprises about two moles of 5,10-methylene-(6R)-tetrahydrofolic acid and/or 5,10-methylene-(6R)-tetrahydrofolate to one mole of sulfate ions.

30. A product according to claim 15, which is a lyophilized formulation D, which
- D) comprises about 1 mole of 5,10-methylene-(6R)-tetrahydrofolic acid and/or 5,10-methylene-(6R)-tetrahydrofolate to one mole of sulfate ions without the presence of citrate.

31. A product according to claim 15, which is a lyophilized formulation E, which
- E) comprises 5,10-methylene-(6R)-tetrahydrofolic acid and/or 5,10-methylene-(6R)-tetrahydrofolate having a chemical purity of greater than 99%, and sulfate with the presence of citrate or without the presence of citrate.

32. A product according to claim 15, which is a stable pharmaceutical composition X comprising
- X) a lyophilised hemisulfate salt of 5,10-methylene-(6R)-tetrahydrofolic acid, which has such stability that the composition maintains greater than or equal to 95% of purity of the 5,10-methylene-(6R)-tetrahydrofolic acid for at least 24 months at +25° C./60% relative humidity; or for at least 12 months at +40° C./75% relative humidity, or for at least 24 months at +5° C., or for at least 24 months at −20° C.

33. A product according to claim 15, which is a stable pharmaceutical composition Y comprising
- Y) a reconstituted lyophilised hemisulfate salt of 5,10-methylene-(6R)-tetrahydrofolic acid, which has such stability that the composition maintains greater than or equal to 95% of purity of the 5,10-methylene-(6R)-tetrahydrofolic acid for at least 200 minutes at 2-8° C., or for at least 2 hours at room temperature.

* * * * *